(12) United States Patent
Kohn et al.

(10) Patent No.: US 7,928,132 B2
(45) Date of Patent: Apr. 19, 2011

(54) METHODS FOR THE AMELIORATION OF EPISODES OF ACUTE OR CHRONIC ULCERATIVE COLITIS

(75) Inventors: Leonard D. Kohn, Athens, OH (US); Douglas J. Goetz, Athens, OH (US); Uruguaysito Benavides-Peralta, Athens, OH (US); Mariana Gonzalez-Murguiondo, Athens, OH (US); Norikazu Harii, Yaminashi (JP); Christopher J. Lewis, Athens, OH (US); Giorgio Napolitano, Pescara (IT); Nilesh D. Dagia, Athens, OH (US)

(73) Assignee: Ohio University, Athens, OH (US)

( * ) Notice: Subject to any disclaimer, the term of this patent is extended or adjusted under 35 U.S.C. 154(b) by 544 days.

(21) Appl. No.: 10/912,948

(22) Filed: Aug. 6, 2004

(65) Prior Publication Data
US 2006/0058365 A1   Mar. 16, 2006

(51) Int. Cl.
*A61K 31/4164* (2006.01)
*A61K 31/4166* (2006.01)
(52) U.S. Cl. .................................. 514/386; 514/398
(58) Field of Classification Search .................. None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni et al. | |
| 3,630,200 A | 12/1971 | Higuchi et al. | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,734,421 A * | 3/1988 | Hammond et al. | 514/274 |
| 5,556,574 A | 9/1996 | Rivas et al. | |
| 6,365,616 B1 | 4/2002 | Kohn et al. | |
| 2005/0209295 A1* | 9/2005 | Kohn et al. | 514/389 |

FOREIGN PATENT DOCUMENTS
WO   00/25756   *   5/2000

OTHER PUBLICATIONS

The Merck Manual, 17th edition (1999), p. 307.*
Isman et al., Journal of Endocrinology (2003), 177(3), 471-476.*
The Merck Manual, 17th edition (1999), pp. 310-311.*
Grisham, M. B., and D. N. Granger. 1999. Leukocyte-endothelial cell interactions in inflammatory bowel disease. In Inflammatory bowel disease. J. B. Kirsner, ed. Saunders, Philadelphia, p. 55-64.
Cario, E., and D. K. Podolsky. 2000. Differential alteration in intestinal epithelial cell expression of toll-like receptor 3 (TLR3) and TLR4 in inflammatory bowel disease. Infect Immun 68:7010-7017.
Singh, U. P., S. Singh, D. D. Taub, and J. W. Lillard, Jr. 2003. Inhibition of IFN-gamma-inducible protein-10 abrogates colitis in IL-10-/- mice. J Immunol 171:1401-1406.
Kobayashi M, Kweon MN, Kuwata H et al. Toll-like receptor-dependent production of IL-12p40 causes chronic enterocolitis in myeloid cell-specific Stat3-deficient mice. J Clin Invest 2003;111(9):1297-308.
Carlos, T. M., and J. M. Harlan. 1994. Leukocyte-endothelial adhesion molecules. *Blood* 84:2068-2101.
Luscinskas, F. W., and M. A. Gimbrone. 1996. Endothelial-dependent mechanisms in chronic inflammatory leukocyte recruitment. *Annu. Rev. Med.* 47:413-421.
Springer, T. A. 1994. Traffic signals for lymphocyte recirculation and leukocyte emigration: the multistep paradigm. *Cell* 76:301-314.
Targan, S. R., S. B. Hanauer, S. J. van Deventer, L. Mayer, D. H. Present, T. Braakman, K. L. DeWoody, T. F. Schaible, and P. J. Rutgeerts. 1997. A short-term study of chimeric monoclonal antibody cA2 to tumor necrosis factor alpha for Crohn's disease. Crohn's Disease cA2 Study Group. *N Engl J Med* 337:1029-1035.
Soriano, A., A. Salas, M. Sans, M. Gironella, M. Elena, D. C. Anderson, J. M. Pique, and J. Panes. 2000. VCAM-1, but not ICAM-1 or MAdCAM-1, immunoblockade ameliorates DSS- induced colitis in mice. *Lab. Invest.* 80:1541-1551.
Wallace, J. L., A. Higa, G. W. McKnight, and D. E. MacIntyre. 1992. Prevention and reversal of experimental colitis by a monoclonal antibody which inhibits leukocyte adherence. *Inflammation* 16:343-354.
Conner, E. M., S. Brand, J. M. Davis, F. S. Laroux, V. J. Palombella, J. W. Fuseler, D. Y. Kang, R. E. Wolf, and M. B. Grisham. 1997. Proteasome inhibition attenuates nitric oxide synthase expression, VCAM-1 transcription and the development of chronic colitis. *J Pharmacol Exp Ther* 282:1615-1622.
Cooper, D. S. 1984. Antithyroid drugs. *N Engl J Med* 311:1353-1362.
Elias, A. N., R. J. Barr, M. K. Rohan, and K. Dangaran. 1995. Effect of orally administered antithyroid thioureylenes on PCNA and P53 expression in psoriatic lesions. *Int J Dermatol* 34:280-283.
Singer, D. S., L. D. Kohn, H. Zinger, and E. Mozes. 1994. Methimazole prevents induction of experimental systemic lupus erythematosus in mice. *J Immunol* 153:873-880.
Chan, C. C., I. Gery, L. D. Kohn, R. B. Nussenblatt, E. Mozes, and D. S. Singer. 1995. Periocular inflammation in mice with experimental systemic lupus erythematosus. A new experimental blepharitis and its modulation. *J Immunol* 154:4830-4835.
Davies, T. F., I. Weiss, and M. A. Gerber. 1984. Influence of methimazole on murine thyroiditis. Evidence for immunosuppression in vivo. *J Clin Invest* 73:397-404.
Wang, P., S. H. Sun, P. B. Silver, C. C. Chan, R. K. Agarwal, B. Wiggert, L. D. Kohn, G. A. Jamieson, Jr., and R. R. Caspi. 2003. Methimazole protects from experimental autoimmune uveitis (EAU) by inhibiting antigen presenting cell function and reducing antigen priming. *J Leukoc Biol* 73:57-64.
Wenisch, C., D. Myskiw, A. Gessl, and W. Graninger. 1995. Circulating selectins, intercellular adhesion molecule-1, and vascular cell adhesion molecule-1 in hyperthyroidism. *J Clin Endocrinol Metab* 80:2122-2126.
Oren, R., Y. Maaravi, F. Karmeli, G. Kenet, L. Zeidel, A. Hubert, and R. Eliakim. 1997. Anti-thyroid drugs decrease mucosal damage in a rat model of experimental colitis. *Aliment Pharmacol Ther* 11:341-345.

(Continued)

*Primary Examiner* — Phyllis G. Spivack
(74) *Attorney, Agent, or Firm* — William J. McNichol; Reed Smith LLP

(57) ABSTRACT

Methods of ameliorating episodes of accute or chronic colitis are provided by using methimazole derivatives and tautomeric cyclic thiones in combination with another pharmaceutical compound.

17 Claims, No Drawings

OTHER PUBLICATIONS

Dagia, N. M., N. Harii, A. E. Meli, X. Sun, C. J. Lewis, L. D. Kohn, and D. J. Goetz. 2004. Phenyl methimazole inhibits TNFα-induced VCAM-1 expression in an IFN Regulatory Factor-1-dependent manner and reduces monocytic cell adhesion to endothelial cells—*J Immunol 173*:2041-2049.

Lange, S., D. S. Delbro, E. Jennische, and I. Mattsby-Baltzer. 1996. The role of the Lps gene in experimental ulcerative colitis in mice. *Apmis 104*:823-833.

Takeda, K., and S. Akira. 2003. Toll receptors and pathogen resistance. *Cell Microbiol 5*:143-153.

Takeda, K., T. Kaisho, and S. Akira. 2003. Toll-like receptors. *Annu Rev Immunol 21*:335-376.

Oshiumi, H., M. Matsumoto, K. Funami; T. Akazawa, and T. Seya. 2003. TICAM-1, an adaptor molecule that participates in Toll-like receptor 3-mediated interferon-beta induction. *Nat Immunol 4*:161-167.

Yamamoto, M., S. Sato, K. Mori, K. Hoshino, O. Takeuchi, K. Takeda, and S. Akira. 2002. Cutting edge: a novel Toll/IL-1 receptor domain-containing adapter that preferentially activates the IFN-beta promoter in the Toll-like receptor signaling. *J Immunol 169*:6668-6672.

Bendjelloul, F., P. Rossmann, P. Maly, V. Mandys, M. Jirkovska, L. Prokesova, L. Tuckova, and H. Tlaskalova-Hogenova. 2000. Detection of ICAM-1 in experimentally induced colitis of ICAM-1-deficient and wild-type mice: an immunohistochemical study. *Histochem J 32*:703-709.

Mabley, J. G., P. Pacher, L. Liaudet, F. G. Soriano, G. Hasko, A. Marton, C. Szabo, and A. L. Salzman. 2003. Inosine reduces inflammation and improves survival in a murine model of colitis. *Am J Physiol Gastrointest Liver Physiol 284*:G138-144.

Suzuki, K., A. Mori, K. J. Ishii, J. Saito, D. S. Singer, D. M. Klinman, P. R. Krause, and L. D. Kohn. 1999. Activation of target-tissue immune-recognition molecules by double-stranded polynucleotides. *Proc Natl Acad Sci U S A 96*:2285-2290.

Dieleman, L. A., M. J. Palmen, H. Akol, E. Bloemena, A. S. Pena, S. G. Meuwissen, and E. P. Van Rees. 1998. Chronic experimental colitis induced by dextran sulphate sodium (DSS) is characterized by Th1 and Th2 cytokines. *Clin Exp Immunol 114*:385-391.

Tuvlin, J. A., and S. V. Kane. 2003. Novel therapies in the treatment of ulcerative colitis. *Expert Opin Investig Drugs 12*:483-490.

Pallone, F., V. Blanco Gdel, P. Vavassori, I. Monteleone, D. Fina, and G. Monteleone. 2003. Genetic and pathogenetic insights into inflammatory bowel disease. *Curr Gastroenterol Rep 5*:487-492.

Panes, J., and D. N. Granger. 1998. Leukocyte-endothelial cell interactions: molecular mechanisms and implications in gastrointestinal disease. *Gastroenterology 114*:1066-1090.

Ortega-Cava, C. F., S. Ishihara, M. A. Rumi, K. Kawashima, N. Ishimura, H. Kazumori, J. Udagawa, Y. Kadowaki, and Y. Kinoshita. 2003. Strategic compartmentalization of Toll-like receptor 4 in the mouse gut. *J Immunol 170*:3977-3985.

Fiocchi, C. 1998. Inflammatory bowel disease: etiology and pathogenesis. *Gastroenterology 115*:182-205.

Kjellin and Sandstrom. Tautomeric Cyclic Thiones; Part II. Preparation of N- and S-Methyl Derivatives of Some Azoline-2-thiones. Acta Chemica Scandanavica 23: 2879-2887 (1969).

Szabo S.J et al. Molecular Mechanisms Regulating Th1 Immune Responses. Annu. Rev. Immunol. 2003. 21:713-58.

* cited by examiner

SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Primer for VCAM-1

<400> SEQUENCE: 1
gactccgtct cattgacttg cagcaccaca g                                31

<210> SEQ ID NO 2
<211> LENGTH: 31
<212> TYPE: DNA
<213> ORGANISM: Artificial Sequence
<220> FEATURE:
<223> OTHER INFORMATION: Primer for VCAM-1

<400> SEQUENCE: 2
atactcccgc atccttcaac tgggcctttc g                                31

<210> SEQ ID NO 3
<211> LENGTH: 30
<212> TYPE: DNA
<213> ORGANISM: Artificial Sequence
<220> FEATURE:
<223> OTHER INFORMATION: Primer for IP-10

<400> SEQUENCE: 3
ccatcagcac catgaaccca agtcctgccg                                  30

<210> SEQ ID NO 4
<211> LENGTH: 30
<212> TYPE: DNA
<213> ORGANISM: Artificial Sequence
<220> FEATURE:
<223> OTHER INFORMATION: Primer for IP-10

<400> SEQUENCE: 4
ggacgtcctc ctcatcgtcg actacactgg                                  30

<210> SEQ ID NO 5
<211> LENGTH: 30
<212> TYPE: DNA
<213> ORGANISM: Artificial Sequence
<220> FEATURE:
<223> OTHER INFORMATION: Primer for IL-1b

<400> SEQUENCE: 5
ctcatctggg atcctctcca gccaagcttc                                  30

<210> SEQ ID NO 6
<211> LENGTH: 30
<212> TYPE: DNA
<213> ORGANISM: Artificial Sequence
<220> FEATURE:
<223> OTHER INFORMATION: Primer for IL-1b

<400> SEQUENCE: 6
ccatggtttc ttgtgaccct gagcgacctg                                  30

METHODS FOR THE AMELIORATION OF EPISODES OF ACUTE OR CHRONIC ULCERATIVE COLITIS This invention was made with government support under Grant Nos. BES 9733542 (0096303) and EHR0227907 awarded by the National Science Foundation. The government may have certain rights in the invention.

TECHNICAL FIELD

The present invention relates to the treatment of inflammatory bowel disease (IBD) and related gastrointestinal pathologies. This invention also relates to the treatment of cytokine-mediated diseases, for example, tumor necrosis factor-α (TNFα)-induced diseases. The invention additionally relates to chemokine-mediated diseases. This invention also relates to treating an animal having a disease or condition associated with abnormal Toll-like receptor 4 (TLR4) expression or signaling. Specifically, the present invention relates to the treatment of inflammatory bowel disease (IBD) and related gastrointestinal pathologies that are cytokine-mediated, chemokine-mediated, or associated with Toll-like receptor 4 expression or signaling.

BACKGROUND OF THE INVENTION

Ulcerative colitis is a chronic inflammatory disease of unknown etiology afflicting the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Signs and symptoms of the disease include cramping, lower abdominal pain, rectal bleeding, and frequent, loose discharges consisting mainly of blood, pus, and mucus with scanty fecal particles. A total colectomy may be required for acute, severe or chronic, unremitting ulcerative colitis.

Neither the initiating event nor the sequence of propagating events that lead to and sustain colitis have been fully elucidated (1). Nevertheless, it is increasingly clear that a dysfunctional immune-response, involving Toll-like receptor 4 (TLR4) and components of normal gastrointestinal gram-negative bacteria appear to play a key role in the pathogenesis of colitis (2). Thus, an early step is macrophage antigen presentation (1), a process involving the CD14/TLR4 complex, which leads to interferon (IFN) production and release, as well as T lymphocyte secretion of IL-2. IFNs activate macrophages to produce a variety of cytokines, including TNFα and IL-1, that upregulate endothelial cell adhesion molecules (ECAMs). Chemokines such as IP-10 are also important in colitis (3) and have been implicated in studies of the myeloid cell-specific Stat3-deficient mouse, which is one of several experimentally induced, Th1-mediated models of Crohn's disease (CD) and UC. The Stat3-deficient mouse model also implicated TLR4 in disease expression, defective IL-10 signaling, and aberrant production of IL-12p40. Pro-inflammatory cytokines activate leukocytes and induce increased expression of ECAMs (5, 6) leading to leukocyte recruitment and extravasation via a well described adhesion cascade (7). Thus, in sum, the aberrant immune/inflammatory response is characterized by increased expression of TLR4, pro-inflammatory cytokines, chemokines, and ECAMs as well as enhanced interactions between leukocytes and hyper-adhesive colonic microvasculature.

Tumor necrosis factor alpha, or TNFα, is a cytokine that is released primarily by mononuclear phagocytes in response to a number of immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions, including: endotoxemia and/or toxic shock syndrome, cachexia, and adult respiratory distress syndrome (ARDS). TNFα appears to be involved in bone resorption diseases, including arthritis. TNFα also plays a role in the area of chronic inflammatory diseases, inducing angiogenesis in inflammation and reperfusion injury following ischemia. TNFα has pro-inflammatory activities, which mediate tissue injury in several important disorders including but not limited to, myocardial infarction, stroke and circulatory shock. Of specific importance may be TNFα-induced expression of adhesion molecules, such as intercellular adhesion molecule-1 (ICAM-1), vascular cell adhesion molecule-1 (VCAM-1) and endothelial leukocyte adhesion molecule-1 (ELAM-1; a/k/a E-selectin), on endothelial cells. TNFα blockage has been shown to be beneficial in rheumatoid arthritis and Crohn's disease.

The above observations have led to the development of several therapeutic approaches that seek to diminish colitis (and related diseases) by attenuating the immune/inflammatory response. These approaches include the use of MAbs to TNFα (8), MAbs to ECAMs (e.g. MAbs to VCAM-1 (9), MAbs to leukocyte β2 integrins (10), and compounds that block the expression of ECAMs at the transcription level (11)).

Methimazole (MMI) is widely used clinically for the treatment of autoimmune Graves' disease or primary hyperthyroidism (12) and has been shown to be effective in treating several other forms of autoimmune disease, including psoriasis in humans (13), systemic lupus (14), autoimmune blepharitis, autoimmune uveitis, thyroiditis, and diabetes in murine experimental models (15-18). Several observations suggest that MMI may also affect ECAM expression and thus could be a potential anti-inflammatory compound. Specifically, it has been reported that (a) Graves' disease patients treated with MMI have reduced levels of circulating soluble E-selectin and soluble VCAM-1 (19) and (b) MMI decreases colonic mucosal damage in a rat model of experimental colitis (20). An effort to identify derivative compounds with greater anti-immune efficacy than MMI, led to the finding that phenyl methimazole (compound 10, C-10), a tautomeric cyclic thione, was 50 to 100-fold more potent and a far more effective agent in experimental models of lupus and diabetes (18, 21).

The observations regarding MMI and C-10 led us to probe the hypothesis that C-10 can reduce pathological inflammation. In a recent study, we used an in vitro model of inflammation and found evidence in support of this hypothesis. Specifically, we found that C-10 can reduce TNFα induced leukocytic cell adhesion to endothelial cells via inhibition of TNFα induced VCAM-1 and E-selectin expression (22). This finding, combined with the fact that TNFα and VCAM-1 have been implicated in the pathogenesis of colitis (1, 8), and the fact that therapies that inhibit the inflammatory cascade have proved quite successful in the treatment of colitis (8, 9), led us to probe the use of C-10 as a therapeutic for colitis. For this study, we used the DSS induced murine model of colitis, which is a well established model of human colitis (23). This model is characterized by dysregulated inflammatory response indicated by presence of edema, infiltration of inflammatory cells, and extensive mucosal damage. We used this model to assess the effect of C-10 on the gross pathology of colitis as well as on the expression of key receptors, cytokines, chemokines and ECAMs that have been implicated in the pathogenesis of colitis.

SUMMARY OF THE INVENTION

The present invention relates to methods for inhibiting cytokine-mediated activity and treatment of cytokine-mediated inflammatory bowel disease and related gastrointestinal pathologies. The present invention also provides for methods of treating a disease mediated by cytokines and chemokines, apparently resultant from induction of a TLR4-mediated innate immune response to products of microorganisms, which comprises administering to a patient in need of such treatment a therapeutically effective amount of one or more compounds of the present invention capable of inhibiting the innate immune response, the cytokines, the chemokines, and the increased VCAM-1.

In one embodiment, the present invention provides for methods of treating a gastrointestinal disorder in a patient in need thereof comprising administering to the patient a therapeutically effective amount of one or more methimazole derivatives and/or tautomeric cyclic thiones. In an additional embodiment, the gastrointestinal disorder is: Crohn's disease, ulcerative colitis, a bowel disease induced by a bacterial infection, indeterminate colitis, infectious colitis, drug or chemical-induced colitis, diverticulitis, ischemic colitis, gastritis, irritable bowel syndrome, a peptic ulcer, a stress ulcer, a bleeding ulcer, gastric hyperacidity, dyspepsia, gastroparesis, Zollinger-Ellison syndrome, gastroesophageal reflux disease, short-bowel (anastomosis) syndrome, a hypersecretory state associated with systemic mastocytosis or basophilic leukemia or hyperhistaminemia. In a further aspect, the present invention concerns the treatment of cytokine-mediated inflammatory bowel disease including: ulcerative colitis, Crohn's, indeterminate colitis, infectious colitis, drug or chemical-induced colitis, diverticulitis, and ischemic colitis. In another embodiment, the present methods provide for the treatment of cytokine-mediated ulcerative colitis.

In another embodiment, the present invention provides for methods of treating a disease mediated by cytokines which comprises administering to a patient in need of such treatment a therapeutically effective amount of one or more methimazole derivatives and/or tautomeric cyclic thiones. The cytokine-mediated disease is selected from the following: acquired immune deficiency syndrome, acute and chronic pain, acute purulent meningitis, adult respiratory distress syndrome (ARDS), Alzheimer's disease, aphthous ulcers, arthritis, asthma, atherosclerosis, atherosclerosisatopic dermatitis, bone resorption diseases, cachexia, chronic obstructive pulmonary disease, congestive heart failure, contact dermatitis, Crohn's disease, dermatoses with acute inflammatory components, diabetes, endotoxemia, glomerulonephritis, graft versus host disease, granulocyte transfusion, Guillain-Barre syndrome, inflammatory bowel disease, leprosy, leukopherisis, malaria, multiple organ injury secondary to trauma, multiple sclerosis, myocardial infarction, necrotizing enterocolitis and syndromes associated with hemodialysis, osteoarthritis, osteoporosis, psoriasis, reperfusion injury following ischemia, restenosis following percutaneous transluminal coronary angioplasty, rheumatoid arthritis, sarcoidosis, scleroderma, sepsis, septic shock, stroke, systemic lupus erythrematosis, thermal injury, toxic shock syndrome, traumatic arthritis, and ulcerative colitis.

In still another aspect, the method involves administering to a patient an effective amount of an agent that decreases the endogenous amount of intracellular or extracellular cytokine, chemokine, or related mediators and a pharmaceutically acceptable carrier or diluent. In another aspect, the cytokine involved in the cytokine-mediated disease or pathology is a pro-inflammatory cytokine. In still another aspect, the pro-inflammatory cytokine is selected from the group that includes, but is not limited to, TNF$\alpha$, IL-1, IL-1$\beta$, IL-6, and IL-8. The chemokine is selected from the group that includes but is not limited to IP-10, MCP-1, RANTES, and SDF-1. The related mediators are selected from a group that includes but is not limited to lipopolysaccharide-biding protein, TLR4, CD-14, GM-CSF, and G-CSF.

The present invention also provides a method of treating a cytokine-mediated disease, which comprises administering an effective cytokine-interfering amount of one or more compounds of the present invention, or a pharmaceutically acceptable salt or tautomer thereof. Compounds of the present invention are useful for, but not limited to, the treatment of any disorder or disease-state in a human, or other mammalian subject, which is exacerbated or caused by excessive or unregulated TNF$\alpha$ production by such mammal. In another embodiment, the methimazole derivative and tautomeric cyclic thione compounds can be used, under the supervision of qualified professionals, to inhibit the undesirable effects of TNF$\alpha$ This invention also relates to pharmaceutical formulations capable of inhibiting tumor necrosis factor-$\alpha$ (TNF$\alpha$)-induced vascular cell adhesion molecule-1 (VCAM-1) expression and the resultant leukocyte-endothelial cell adhesion for the inhibition and prevention of ulcerative colitis and related gastrointestinal pathologies. In particular, the methimazole derivatives and tautomeric cyclic thiones are suitable for the treatment of diseases that are caused at least partly by an undesired extent of tumor necrosis factor-$\alpha$ (TNF$\alpha$)-induced vascular cell adhesion molecule-1 (VCAM-1) expression and resultant leukocyte-endothelial cell adhesion or are connected therewith, and for whose prevention, alleviation or cure the TNF$\alpha$-induced VCAM-1 expression and resultant leukocyte-endothelial cell adhesion should be decreased.

In one embodiment, the present invention provides for methods for reducing aberrant tumor necrosis factor-$\alpha$ (TNF$\alpha$)-induced vascular cell adhesion molecule-1 (VCAM-1) expression and resultant leukocyte-endothelial cell adhesion during pathological inflammation by inhibiting TNF$\alpha$-induced VCAM-1 expression at the transcriptional level. Specifically, the present invention provides for methods of using methimazole derivatives or tautomeric cyclic thiones to modulate TNF$\alpha\alpha$-induced VCAM-1 expression and consequent leukocyte-endothelial cell adhesion.

The present invention also involves compositions and methods that inhibit TNF$\alpha$ release and/or activity in vivo, for the treatment of any conditions involving a TNF$\alpha$-induced diseases or pathology, which include but are not limited to: shock, including endotoxin-induced sepsis, severe sepsis, and septic shock, inflammation, graft versus host disease, autoimmune diseases, acute respiratory distress syndrome, granulomatous diseases, chronic infections, transplant rejection, cachexia, bacterial infections, viral infections, parasitic infections, fungal infections, and/or trauma. Also included are diseases mediated by microbial toxins including Gram-negative bacterial endotoxin, Gram-positive bacterial endotoxins, toxins of other microbial or infectious agents, and cell wall fragments of microbial pathogens such as peptidoglycan and lipoteichoic acids. TNF$\alpha$ acts to regulate inflammation and immunity, and plays a role in the development of a primary immune response. In particular, TNF$\alpha$ potentiates lethality of endotoxemia, whereas the inhibition of TNF$\alpha$ confers protection against lethal endotoxemia. Inhibition of TNFα similarly confers protection against toxic shock syndrome. The inhibition of TNFα activity and/or release may be used to treat inflammatory response and shock. Beneficial effects may be achieved by intervention at both early and late stages of the shock response.

In another aspect, the invention is concerned with a method for treating an inflammatory or infectious condition or disease by administering a therapeutically effective amount of an agent that decreases the endogenous amount of intracellular or extracellular cytokine to a patient suffering from the inflammatory condition or disease. One skilled in the art will recognize that the term "an inflammatory or infectious condition or disease" includes, but is not limited to: autoimmune or inflammatory diseases such as multiple sclerosis, inflammatory bowel disease, insulin dependent diabetes mellitus, and rheumatoid arthritis, trauma, chemotherapy reactions, transplant rejections the generalized Schwarzmann reaction, system inflammatory response syndrome, sepsis, severe sepsis, or septic shock.

In a further aspect, the invention concerns a method for treating a disease such as graft versus host disease, acute respiratory distress syndrome, granulomatous disease, transplant rejection, cachexia, parasitic infections, fungal infections, trauma, and bacterial infections by administering a therapeutically effective amount of an agent that decreases the endogenous amount of intracellular or extracellular TNFα to a patient suffering from the disease.

The present invention also involves compositions and methods that inhibit chemokine release and/or activity in vivo, for the treatment of any conditions involving a chemokine-mediated diseases or pathology.

The present invention also relates to methods for inhibiting chemokine-mediated activity and treatment of chemokine-mediated pathologies. It is one objective to use compounds of the present invention to treat chemokine mediated diseases selected from the group consisting of psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral and cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus, meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred and corneal neovascularization, polymyositis, vasculitis, acne, gastric and duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, systemic lupus erythematosus, burn therapy, periodontitis and early transplantation.

The present invention also relates to methods for inhibiting chemokine-mediated activity and treatment of chemokine-mediated diseases where the chemokine-mediated disease is a pulmonary disease selected from COPD, asthma or cystic fibrosis. In another embodiment, the compounds of the present invention are administered in conjunction with one or more drugs, agents or therapeutics selected from the group consisting of: glucocorticoids, 5-lipoxygenase inhibitors, α-2 adrenoceptor agonists, muscarinic M1 and M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, growth hormones, and transcription inhibitors (e.g., proteasome inhibitor PS-519).

The present invention relates to methods for inhibiting chemokine-mediated activity and treatment of chemokine-mediated inflammatory bowel disease and related gastrointestinal pathologies. The present invention provides a method of treating a chemokine-mediated disease, which comprises administering an effective chemokine-interfering amount of one or more compounds of the present invention, or a pharmaceutically acceptable salt or tautomer thereof. Compounds of the present invention are useful for, but not limited to, the treatment of any disorder or disease-state in a human, or other mammal, which is exacerbated or caused by excessive or unregulated chemokine production by such mammal. In another embodiment, the methimazole derivative and tautomeric cyclic thione compounds can be used, under the supervision of qualified professionals, to inhibit the undesirable effects of chemokines.

In a further aspect, the present invention concerns the treatment of chemokine-induced inflammatory bowel disease, including ulcerative colitis, Crohn's, indeterminate colitis, infectious colitis, drug or chemical-induced colitis, diverticulitis, and ischemic colitis. In another embodiment, the present methods provide for the treatment of chemokine-induced colitis.

In one embodiment, this aspect additionally involves administering a therapeutic steroid to the patient. By way of non-limiting example, therapeutic steroids may include, for example, corticoids, glucocorticoids, dexamethasone, prednisone, prednisolone, and betamethasone. In a further aspect, the invention concerns a method for enhancing the anti-inflammatory activity of a therapeutic steroid or reducing the toxic side effects of a therapeutic steroid by administering a therapeutically effective amount of an agent that decreases the endogenous amount of intracellular or extracellular cytokine or chemokine in an individual in need of such treatment.

In another aspect, the invention involves a method for treating a condition involving a cytokine-induced diseases or pathology by administering to a patient an effective amount of an agent that down-regulates a Toll-like receptor (TLR) or its signaling. In one embodiment, the agent that down-regulates the Toll-like receptor signaling does so by decreasing the endogenous amount of intracellular or extracellular cytokines.

The present invention also provides compositions and methods for modulating the expression of Toll-like receptor 4 (TLR4). In another aspect, the invention involves a method for inhibiting the expression of Toll-like receptor 4 (TLR4) in cells or tissues comprising contacting said cells or tissues with one or more of the compounds of the present invention so that expression of Toll-like receptor 4 (TLR4) is inhibited. In another aspect, the invention involves a method for treating an animal having a disease or condition associated with overexpression of Toll-like receptor 4 comprising administering to the animal a therapeutically or prophylactically effective amount of one or more methimazole derivative and tautomeric cyclic thione compounds of the present invention so that expression of Toll-like receptor 4 is inhibited.

Further provided are methods for treating a condition involving a cytokine-induced disease or pathology comprising administering to a patient an effective amount of an agent that down-regulates a Toll-like receptor. Preferably, the Toll-like receptor is Toll-like receptor 4. In another embodiment, the method further comprises administering a therapeutic steroid. In another embodiment, the agent that down-regulates the Toll-like receptor decreases the endogenous amount of intracellular or extracellular cytokine.

Further provided are methods of treating an animal having a disease or condition associated with Toll-like receptor 4 comprising administering to the animal a therapeutically or prophylactically effective amount of one or more of the compounds of the present invention so that abnormal expression of Toll-like receptor 4 and its signal is inhibited. Also provided are methods of inhibiting the expression of Toll-like receptor 4 in cells or tissues comprising contacting the cells or tissues with one or more of the compounds of the present invention so that expression of Toll-like receptor 4 or its signal is inhibited. In one embodiment, the condition is an inflammatory disorder.

The present invention relates to methods for inhibiting Toll-like receptor-4 ("TLR-4") activity and treatment of Toll-like receptor 4 induced inflammatory bowel disease and related gastrointestinal pathologies. In a further aspect, the present invention concerns the treatment of Toll-like receptor 4 induced inflammatory bowel disease, including ulcerative colitis, Crohn's, indeterminate colitis, infectious colitis, drug or chemical-induced colitis, diverticulitis, and ischemic colitis. In another embodiment, the present methods provide for the treatment of Toll-like receptor 4 induced colitis.

It is one object of the present invention to provide methods for inhibiting the biological activity of TLR4, as, for example, by inhibiting its expression or signaling. It is a further object of the invention to provide methods of treating those diseases in which inhibiting TLR-4 would have a beneficial effect.

In one embodiment, the Toll-like receptor 4 associated disease is one or more of systemic lupus erythematosis, scleroderma, Sjogren's syndrome, multiple sclerosis and other demyelinating diseases, rheumatoid arthritis, juvenile arthritis, myocarditis, uveitis, Reiter's syndrome, gout, osteoarthritis, polymyositis, primary biliary cirrhosis, inflammatory bowel disease, Crohn's disease, ulcerative colitis, aplastic anemia, Addison's disease, insulin-dependent diabetes mellitus, endotoxic shock, and other diseases.

In an alternate embodiment, methods of the present invention are used to inhibit the Toll-like receptor 4-mediated innate immune disease including atherosclerosis, transplant atherosclerosis, vein-graft atherosclerosis, stent restenosis, and angioplasty restenosis, and to thereby treat the cardiovascular diseases that atherosclerosis causes (hereinafter "vascular diseases"). These methods may be used in any patient who could benefit from reducing atherosclerosis that is already present, from inhibiting atherosclerosis that has yet to form, or from both reducing existing atherosclerosis and inhibiting new atherosclerosis. Such patients include those suffering from, for example, angina pectoris and its subtypes (e.g., unstable angina and variant angina); ischemias affecting organs such as the brain, heart, bone, and intestines, and conditions associated with the ischemias, such as stroke, transient ischemic attacks, heart attack, osteonecrosis, colitis, poor kidney function, and congestive heart failure; poor blood circulation to the extremities and the complications of poor blood circulation, such as slow wound healing, infections, and claudication; atherosclerosis itself, including restenosis following angioplasty or stenting of atherosclerotic lesions; vein-graft atherosclerosis following bypass surgery; transplant atherosclerosis; and other diseases caused by or associated with atherosclerosis.

In another embodiment, such diseases include, for example, vascular diseases such as atherosclerosis and thrombosis, restenosis after angioplasty and/or stenting, and vein-graft disease after bypass surgery.

The present compounds may also be used in co-therapies, partially or completely, in place of other conventional anti-inflammatories, such as together with steroids, cyclooxygenase-2 inhibitors, NSAIDs, DMARDS, antibiotics, immunosuppressive agents, 5-lipoxygenase inhibitors, $LTB_4$ antagonists and $LTA_4$ hydrolase inhibitors and anti-cell adhesion molecules, such as anti E-selectin.

In another embodiment, the present invention provides for methods for reducing inflammation caused by a gastrointestinal inflammatory disease. In another embodiment, the present invention provides for methods for treating a subject suffering from an inflammatory condition involving the large intestine. In another embodiment, the inflammatory condition involving the large intestine is selected from the group comprising Crohn's disease, ulcerative colitis, infectious colitis, drug or chemical-induced colitis, diverticulitis, and ischemic colitis. In another embodiment, the subject has undergone partial or subtotal resection of the large intestine. In another embodiment, the methods are used prophylactically to treat a subject at risk of developing an inflammatory condition of the intestine involving inflammation of the large intestine.

The present invention relates to therapeutics for the prevention and treatment of ulcerative colitis. Specifically, the present invention contemplates the prevention and treatment of ulcerative colitis in humans as well as other animals through the use of methimazole derivatives and tautomeric cyclic thiones. It is not intended that the present invention be limited to a particular type of methimazole derivative or tautomeric cyclic thione.

In another embodiment, the present invention contemplates a method of relieving symptoms of and rescuing mammals (including humans) from episodes of acute or chronic ulcerative colitis utilizing methimazole derivatives and tautomeric cyclic thiones. The present invention further teaches treatments comprising methimazole derivatives and tautomeric cyclic thiones and methods used after the onset of symptoms of ulcerative colitis.

In another embodiment, the present invention contemplates a method of relieving symptoms of and rescuing-mammals (including humans) from episodes of acute or chronic ulcerative colitis utilizing a combination comprising methimazole derivatives and tautomeric cyclic thiones in combination with salicylates (including sulfasalazine, olsalazine, and mesalamine), corticosteroids, immunosuppressants (including azathioprine and 6-mercaptopurine), antibiotics, anti adhesion molecules such as anti E-selectin, and a vitamin D compound (e.g., 1-alpha,25-dihydroxyvitamin $D_3$).

The present invention contemplates a method of treatment, comprising: (a) providing i) a mammal for treatment; ii) a therapeutic preparation, comprising methimazole derivatives and tautomeric cyclic thiones and (b) administering the methimazole derivatives and tautomeric cyclic thiones to the mammal.

In another embodiment, the present invention also contemplates a method of treatment, comprising: a) providing: i) a human patient with symptoms of inflammatory bowel disease, ii) a therapeutic formulation comprising a methimazole derivatives and tautomeric cyclic thiones, and; b) administering said formulation to said patient.

In another embodiment, the present invention also contemplates a method of treatment, comprising: a) providing: i) a human patient with symptoms of ulcerative colitis, ii) a therapeutic formulation comprising methimazole derivatives and tautomeric cyclic thiones, and; b) administering said formulation to said patient.

In the above embodiments, it is preferred that said administering is done under conditions such that the symptoms of ulcerative colitis are reduced.

According to one embodiment of this invention, these novel compounds, compositions and methods are advantageously used for treatment and prevention of ulcerative colitis and related gastrointestinal pathologies. The present invention also provides methods for preparing the compounds of this invention and intermediates useful in those methods.

In one embodiment, the present invention provides for the use of methimazole (1-methyl-2-mercaptoimidazole) and its derivatives. In another embodiment, the present invention provides for the use of a prodrug form of methimazole, known as carbimazole (neomercazole) and its derivatives.

In another embodiment, the present invention provides for the use of a composition containing one or more of the compounds selected from the group consisting of: methimazole, metronidazole, 2-mercaptoimidazole, 2-mercaptobenzimidazole, 2-mercapto-5-nitrobenzimidazole, 2-mercapto-5-methylbenzimidazole, s-methylmethimazole, n-methylmethimazole, 5-methylmethimazole, 5-phenylmethimazole, and 1-methyl-2-thiomethyl-5(4)nitroimidazole. Preferably, 5-phenylmethimazole is used.

In another embodiment, the present invention provides for the use of phenyl methimazole (compound 10; C-10) and its derivatives for the treatment ulcerative colitis and related gastrointestinal pathologies.

Compounds of this invention may be synthesized using any conventional technique. Preferably, these compounds are chemically synthesized from readily available starting materials.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Once synthesized, the activities and specificities of the compounds according to this invention may be determined using in vitro and in vivo assays.

For example, the treatment of inflammatory bowel disease inhibitory activity of these compounds may be measured in vivo, e.g. by rectal bleeding, bloody stools, pain, colonoscopy, weight loss, colon length, histologic analysis of the colon, levels of circulating cytokines or chemokines, levels of circulating antigens or antibodies, immunocytochemistry, PCR of extracts from colonic cells in the circulation or released into the colonic lumen naturally or obtained surgically, or analysis of circulating immune cells, e.g. mononuclear leukocytes, T-cells or TH-1 helper cells. In in vitro assays, for example, cell adhesion inhibitory activity of these compounds may be measured by determining the concentration of inhibitor required to block the binding of VCAM-1-expressing epithelial or endothelial cells to VCAM-1 ligand (e.g., VLA-4) expressing cells (e.g., monocytes, lymphocytes) from patients or in continuous culture. In this assay, microtiters wells are coated with cells (e.g., epithelial or endothelial cells), which can express VCAM-1. Once the wells are coated, varying concentrations of the test compound are then added together with a cytokine (e.g., TNFα), which can induce the expression of VCAM-1. Alternatively, the test compound may be added first and allowed to incubate with the coated wells containing epithelial or endothelial cells prior to the addition of the cytokine. The cells are allowed to incubate in the wells for at least 2 hrs. Following incubation, appropriately labeled VCAM-1 ligand-expressing cells (e.g., monocytes, lymphocytes) are added to the wells and incubated for at least 30 minutes. After the incubation period, the wells are washed. Inhibition of binding is measured by quantitating the fluorescence or radioactivity bound to the VCAM-1 expressing cells in the plate for each of the various concentrations of test compound, as well as for controls containing no test compound. VCAM-1-expressing cells that may be utilized in this assay include nonimmune target tissue cells, such as colonic cells. The VCAM-1 ligand expressing cells (e.g., monocytes, lymphocytes) used in this assay may be fluorescently or radioactively labeled. Measurements of other cytokines, chemokines, or TLR4 RNA or protein by PCR or antibody-based assays, respectively, could also be used. A direct binding assay may also be employed to quantitate the inhibitory activity of the compounds of this invention.

Once specific inhibitors are identified, they may be further characterized in in vivo assays. One such assay tests the effects of inhibitors in other well-established in vivo models of pathological inflammation (e.g., inflamed mesenteric endothelium in murine model of chronic inflammation (i.e., colitis); isolated carotid arteries of apolipoprotein E-deficient (apoE −/−) mice with developing atherosclerotic lesions).

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Throughout this document, all temperatures are given in degrees Celsius, and all percentages are weight percentages unless otherwise stated. All publications mentioned herein are incorporated herein by reference for the purpose of describing and disclosing the compositions and methodologies, which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

In the following description of the illustrated embodiments, references are made to drawings (Not shown). It is to be understood that other embodiments may be utilized, and structural and functional changes may be made without departing from the scope of the present invention.

DETAILED DESCRIPTION OF THE INVENTION

Before the present device and methods for tissue augmentation is described, it is to be understood that this invention is not limited to the specific methodology, devices, formulations, and compositions described as such may, of course, vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and", and "the" include plural referents unless the context clearly dictates otherwise. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

As used herein, the following terms shall have the definitions given below.

The term "administration" of the pharmaceutically active compounds and the pharmaceutical compositions defined herein includes systemic use, as by injection (especially parenterally), intravenous infusion, suppositories and oral administration thereof, as well as topical application of the compounds and compositions. Oral administration is particularly preferred in the present invention.

"Ameliorate" or "amelioration" means a lessening of the detrimental effect or severity of the disorder in the subject receiving therapy, the severity of the response being determined by means that are well known in the art.

"Chemokines" are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include RANTES, MIP-1α, MIP-2β, monocyte chemotactic protein-1 (MCP-1), MCP-2, MCP-3 and eotaxin.

By "compatible" herein is meant that the components of the compositions which comprise the present invention are capable of being commingled without interacting in a manner which would substantially decrease the efficacy of the pharmaceutically active compound under ordinary use conditions.

By "corticosteroid" is meant any naturally occurring or synthetic steroid hormone which can be derived from cholesterol and is characterized by a hydrogenated cyclopentanoperhydrophenanthrene ring system. Naturally occurring corticosteriods are generally produced by the adrenal cortex. Synthetic corticosteriods may be halogenated. Functional groups required for activity include a double bond at Δ4, a C3 ketone, and a C20 ketone. Corticosteroids may have glucocorticoid and/or mineralocorticoid activity.

Exemplary corticosteroids include, for example, dexamethasone, betamethasone, triamcinolone, triamcinolone acetonide, triamcinolone diacetate, triamcinolone hexacetonide, beclomethasone, dipropionate, beclomethasone dipropionate monohydrate, flumethasone pivalate, diflorasone diacetate, fluocinolone acetonide, fluorometholone, fluorometholone acetate, clobetasol propionate, desoximethasone, fluoxymesterone, fluprednisolone, hydrocortisone, hydrocortisone acetate, hydrocortisone butyrate, hydrocortisone sodium phosphate, hydrocortisone sodium succinate, hydrocortisone cypionate, hydrocortisone probutate, hydrocortisone valerate, cortisone acetate, paramethasone acetate, methylprednisolone, methylprednisolone acetate, methylprednisolone sodium succinate, prednisolone, prednisolone acetate, prednisolone sodium phosphate, prednisolone tebutate, clocortolone pivalate, dexamethasone 21-acetate, betamethasone 17-valerate, isoflupredone, 9-fluorocortisone, 6-hydroxydexamethasone, dichlorisone, meclorisone, flupredidene, doxibetasol, halopredone, halometasone, clobetasone, diflucortolone, isoflupredone acetate, fluorohydroxyandrostenedione, flumethasone, diflorasone, fluocinolone, clobetasol, cortisone, paramethasone, clocortolone, prednisolone 21-hemisuccinate free acid, prednisolone metasulphobenzoate, and triamcinolone acetonide 21-palmitate. By "low dose corticosteroid" is meant a dose that is less than a dose that would typically be given to a patient for treatment of inflammation. Exemplary low doses of corticosteroids are as follows: cortisol: 12 mg/day; cortisone: 15 mg/day; prednisone: 3 mg/day; methylprednisolone: 2.5 mg/day; triameinolone: 2.5 mg/day; betamethasone: 250 μg/day; dexamethasone: 450 μg/day; hydrocortisone: 9 mg/day.

"Crohn's disease" can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

"Inflammatory bowel diseases" ("IBD") are defined by chronic, relapsing intestinal inflammation of obscure origin. Inflammatory bowel disease includes ulcerative colitis, Crohn's disease, indeterminate colitis, infectious colitis, drug or chemical-induced colitis, diverticulitis, and ischemic colitis. These diseases appear to result from the unrestrained activation of an inflammatory response in the intestine. In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. The clinical symptoms of IBD are intermittent rectal bleeding, crampy abdominal pain, weight loss and diarrhea. Diagnosis of IBD is based on the clinical symptoms, the use of a barium enema, but direct visualization (signioidoscopy or colonoscopy) is the most accurate test. Protracted IBD is a risk factor for colon cancer, and treatment of IBD can involve medications and surgery.

As used herein, the term "subject suspected of having inflammatory bowel disease" means any animal capable of having ulcerative colitis, Crohn's disease, or chronic relapsing bowel inflammation including a human, non-human primate, rabbit, rat or mouse, especially a human, and having one or more symptoms of ulcerative colitis, Crohn's disease, or chronic relapsing bowel inflammation.

As used herein, the term "ulcerative colitis" or "UC" mean a disease having clinical features of left-sided colonic disease accompanied by a characteristic endoscopic or histopathologic feature of ulcerative colitis. Clinical features of left-sided colonic disease, as used herein, are rectal bleeding, urgency and tenesmus. The rectal bleeding may be accompanied by mucus discharge. Additional clinical features that may be present in UC include fever, uveitis, rheumatoid arthritis, and other immune/inflammatory diseases or complications. A causal factor for gastrointestinal damage in ulcerative colitis (UC) is a dysregulated, cytokine-mediated, inflammatory response involving leukocytes and specific endothelial cell adhesion molecules (ECAMs). The present invention provides for a novel therapeutic approach to suppress ulcerative colitis and related gastrointestinal pathologies.

A characteristic endoscopic feature of ulcerative colitis, which when present with clinical features of left-sided colonic disease indicates ulcerative colitis, is inflammation that is more severe distally than proximally or continuous inflammation. Additional typical endoscopic features that may be present in ulcerative colitis include inflammation extending proximally from the rectum or shallow ulcerations or the lack of deep ulcerations.

As used herein, the term "patient with ulcerative colitis" means a patient having ulcerative colitis, as defined by the presence of clinical features of left-sided colonic disease accompanied by a characteristic endoscopic or histopathologic feature of ulcerative colitis as defined herein.

The term "clinical subtype of ulcerative colitis," as used herein, means a subgroup of patients having ulcerative colitis whose features of disease are more similar to each other than to other patients with ulcerative colitis.

The phrase "symptoms of ulcerative colitis" is herein defined to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The phrase "wherein said symptoms are reduced" refers to a qualitative or quantitative reduction in detectable symptoms, including but not limited to a detectable impact on the rate of recovery from disease (e.g. rate of weight gain).

The phrase "at risk for ulcerative colitis" is herein defined as encompassing the segment of the world population that has an increased risk for ulcerative colitis. The present invention contemplates administration to or at the lumen as one possibility. The phrase "administered to or at the lumen" or the like is herein defined as delivery to the space in the interior of the intestines. Such delivery can be achieved by a variety of routes (e.g., oral, rectal, etc.) in a variety of vehicles (e.g., tablet, suppository, etc.). In one embodiment, administration to or at the lumen results in delivery of methimazole derivatives and tautomeric cyclic thiones to the lamina propria (or regions of the intestinal wall or radial to the mucosa). The lamina propria is classified as a loose, areolar, connective tissue but with lymphatic tendencies, the lymphoid material presumably functioning as a defense barrier against bacterial infection.

The term "patient", as used herein, is intended to encompass any mammal, animal or human subject, which may benefit from treatment with the compounds, compositions and methods of the present invention.

"Pharmaceutically-acceptable" shall mean that the pharmaceutically active compound and other ingredients used in the pharmaceutical compositions and methods defined herein are suitable for use in contact with the tissues of humans and lower animals without undue toxicity, irritation, allergic response, and the like, commensurate with a reasonable benefit/risk ratio.

The term "prodrug" indicates a therapeutic agent that is prepared in an inactive form that is converted to an active form (i.e., drug) within the body or cells thereof by the action of endogenous enzymes or other chemicals and/or conditions.

The phrase "safe and effective amount" means a sufficient amount of pharmaceutically active compound to effect the inhibition of TLR4-mediated disease expression, abnormal cytokine or chemokine production, and prevention of cell adhesion and cell adhesion-mediated pathologies. Within the scope of sound medical judgement, the required dosage of a pharmaceutically active agent or of the pharmaceutical composition containing that active agent will vary with the severity of the condition being treated, the duration of the treatment, the nature of adjunct treatment, the age and physical condition of the patient, the specific active compound employed, and like considerations discussed more fully hereinafter. In arriving at the "safe and effective amount" for a particular compound, these risks must be taken into consideration, as well as the fact that the compounds described herein provide pharmaceutical activity at lower dosage levels than conventional methimazole compounds.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

"Toll-like receptors" or "TLRs" are type I transmembrane proteins containing repeated leucine-rich motifs in their extracellular domains and a cytoplasmic tail that contains a conserved region called the Toll/IL1 receptor (TIR) domain. At least 10 mammalian TLR proteins have been identified, Toll-like receptors 1-10. TLRs play a critical role in early innate immunity to invading pathogens by sensing microorganisms. These evolutionarily conserved receptors, homologues of the Drosophila Toll gene, recognize highly conserved structural motifs only expressed by microbial pathogens, called pathogen-associated microbial patterns (PAMPs). PAMPs include various bacterial cell wall components such as lipopolysaccharide (LPS), peptidoglycan (PGN) and lipopeptides, as well as flagellin, bacterial DNA and viral double-stranded RNA. TLR thus protect mammals from pathogenic organisms, such as viruses or bacteria, by generating an "innate immune" response to products of the pathogenic organism (24-27). The innate immune response results in increases in genes for several inflammatory cytokines, as well as co-stimulatory molecules, and is critical for the development of antigen-specific adaptive immunity (24-27). Stimulation of TLRs by PAMPs initiates a signaling cascade that involves a number of proteins, such as MyD88 and IRAK1. This signaling cascade leads to the activation of the transcription factor NF-kB which induces the secretion of pro-inflammatory cytokines (such as TNF α and IL1) and effector cytokines that direct the adaptive immune response. TLR-4 specifically recognizes LPS. TLR are present in most monocytes, macrophages, or immune cells; however, although in humans, TLR4 were believed to be restricted to dendritic cells only. TLR4 mRNA has recently been recognized in intestinal epithelial cells associated with inflammatory bowel disease. However, it is unclear whether the RNA encodes a functional receptor that generates a signal inducing APC formation, whether this is a primary action of the intestinal epithelial cell that causes lymphoid cells to target to the tissue, or whether it is a secondary response to the immune cell infiltration.

In specific and in relationship to diseases of the bowel, TLR4 recognizes bacterial lipopolysaccharides from gram negative bacteria that comprise the intestinal flora (24-27). TLR4 activates two distinct pathways (24-27). The first signals through the adapter molecule, MyD88, to activate NFκB, MAPK, and various cytokines (24-27). The second couples through an adapter molecule, termed TIR domain-containing molecule adapter inducing IFN-β/TIR-containing adapter molecule (TRIF/TICAM)-1 (24-27), to activate IFN regulatory factor (IRF)-3 and causes the synthesis and release of type I IFNs (α or β). The type I IFN can induce a positive feedback loop, further upregulating TLR4, or interact with other cells, a phenomenon closely linked to their anti-viral gene defense program. Ligand engagement of the TLRs thus results in activation of NF-κB and induction of the cytokines and co-stimulatory molecules required for the activation of the adaptive immune response as well as Type 1 interferon. Human Toll-like receptor 4 (also known as TLR4 and hToll), the human homolog to the Drosophila protein known as Toll, was cloned from a human fetal liver/spleen library, characterized, and mapped to chromosome 9q32-33. Toll-like receptor 4 mRNA expression can be detected in the cells of the immune system: monocytes, macrophages, dendritic cells, γΔ T-cells, Th1 and Th2 αβ T-cells, and B-cells. Expression has also been detected in intestinal epithelium, thyrocytes, cardiac myocytes and placenta.

"Treat," "treating," "treatment," and "therapy" as used herein refer to any curative therapy, prophylactic therapy, ameliorative therapy and preventative therapy for a subject.

The present invention relates to the treatment of inflammatory bowel disease (IBD) and related gastrointestinal pathologies. This invention also relates to the treatment of cytokine-mediated diseases, including tumor necrosis factor-α (TNFα)-induced diseases and chemokine-induced diseases. This invention also relates to treating an animal having a disease or condition associated with Toll-like receptor 4. Specifically, the present invention relates to the treatment of inflammatory bowel disease (IBD) and related gastrointestinal pathologies that are cytokine-mediated or associated with Toll-like receptor 4. The present invention also provides for methods of treating such disease comprising administering to a patient in need of such treatment a therapeutically effective amount of one or more compounds of the present invention capable of inhibiting pathologies that are cytokine-mediated, chemokine-mediated, or associated with Toll-like receptor 4 overexpression or signaling.

The pharmaceutical compositions of the present invention comprise specifically defined methimazole derivatives and tautomeric cyclic thiones, used in a safe and effective amount, together with a pharmaceutically acceptable carrier.

The methimazole derivatives used in the compositions of the present invention are those having the following structural formulae:

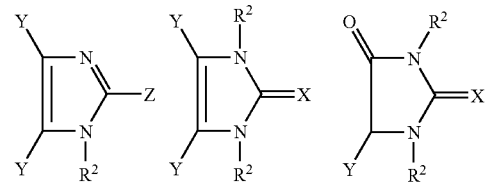

In these formulae, Y is selected from H, $C_1$-$C_4$ alkyl $C_1$-$C_4$ substituted alkyl, —$NO_2$, and the phenyl moiety:

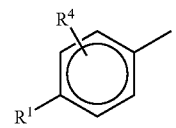

wherein no more than one Y group in said active compound may be the phenyl moiety; $R^1$ is selected from H, —OH, halogens (F, Cl, Br or I), $C_1$-$C_4$ alkyl, $C_1$-$C_4$ substituted alkyl, $C_1$-$C_4$ ester or $C_1$-$C_4$ substituted ester; $R^2$ is selected from H, $C_1$-$C_4$ alkyl or $C_1$-$C_4$ substituted alkyl; $R^3$ is selected from H, $C_1$-$C_4$ alkyl, $C_1$-$C_4$ substituted alkyl or —$CH_2Ph$ (wherein Ph is phenyl); $R^4$ is selected from H, $C_1$-$C_4$ alkyl or $C_1$-$C_4$ substituted alkyl; X is selected from S or O; Z is selected from —$SR^3$, —$OR^3$, $S(O)R^3$ or $C_1$-$C_4$ alkyl; and wherein at least two of the $R^2$ and $R^3$ groups on said compound are $C_1$-$C_4$ alkyl when Y is not a phenyl moiety, and at least one Y is —$NO_2$ when Z is alkyl; together with a pharmaceutically-acceptable carrier.

Y is preferably H, the phenyl moiety or —$NO_2$, and is most preferably H or the phenyl moiety

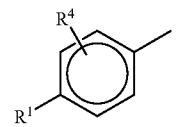

In the defined compounds, no more than one Y group may be the phenyl moiety. $R^1$ is selected from H, —OH, halogens (F, Cl, Br and I), $C_1$-$C_4$ alkyl, $C_1$-$C_4$ substituted alkyl, $C_1$-$C_4$ester and $C_1$-$C_4$ substituted ester; preferably $R^1$ is H, —OH, halogen, —$OOCCH_2M$ (where M is H or a halogen); and is most preferably H. $R^2$ is selected from H, $C_1$-$C_4$ alkyl and $C_1$-$C_4$ substituted alkyl; preferably one or both of the $R^2$ groups is methyl. As used herein, "substituted alkyl" or "substituted ester" is intended to include alkyl, aryl or ester groups which are substituted in one or more places with hydroxyl or alkoxyl groups, carboxyl groups, halogens, nitro groups, amino or acylamino groups, and mixtures of those moieties. Preferred "substituted alkyl" groups are $C_1$-$C_4$ hydroxyl or alkoxyl groups, as well as groups substituted with halogens. The $R^3$ groups in the above formulae are selected from H, $C_1$-$C_4$ alkyl, $C_1$-$C_4$ substituted alkyl and —$CH_2Ph$ (wherein Ph is phenyl); in preferred compounds, $R^3$ is H or $C_1$-$C_4$ alkyl; most preferably $R^3$ is $C_1$-$C_4$ alkyl, particularly methyl. $R^4$ is selected from H, $C_1$-$C_4$ alkyl and $C_1$-$C_4$ substituted alkyl, and preferably is H. X may be S or O, and is preferably S. Finally, Z is selected from $C_1$-$C_4$ alkyl, —$SR^3$, —$S(O)R^3$ and —$OR^3$, is preferably —$SR^3$, —$OR^3$, and —$S(O)R^3$; most preferably —$SR^3$ and —$OR^3$; and particularly —$SR^3$. In the above formulae, at least two of the $R^2$ and $R^3$ groups on the compound must be $C_1$-$C_4$ alkyl when Y is not a phenyl moiety. Further, at least one of the Y groups should be —$NO_2$, when Z is $C_1$-$C_4$ alkyl.

Compounds useful in the present invention include the tautomeric cyclic thiones, disclosed in Kjellin and Sandstrom, Acta Chemica Scandanavica 23: 2879-2887 (1969), incorporated herein by reference, having the formulae

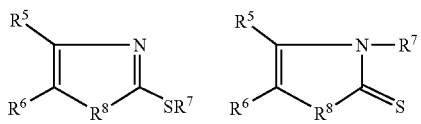

wherein $R^5$, $R^6$=$CH_3$, $CH_3$; Ph, H; H, Ph
$R^7$=H, $CH_3$
$R^8$=O, S, NH, $NCH_3$ Preferred compounds for use in the compositions of the present invention include those having the formulae:

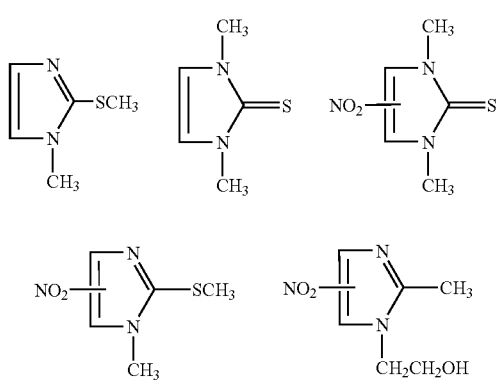

Another group of preferred compositions include those having the formulae:

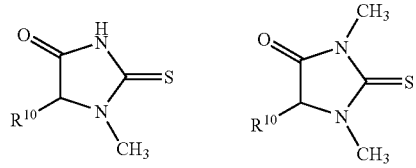

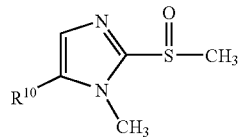

wherein $R^{10}$ is selected from H. $NO_2$, Ph, 4-HOPh and 4-m-Ph (wherein m is F, Cl, Br, or I).

A particularly preferred subset of the pharmaceutical compounds defined herein are those wherein one of the Y groups is the phenyl moiety defined above. These compounds have the following formulae:

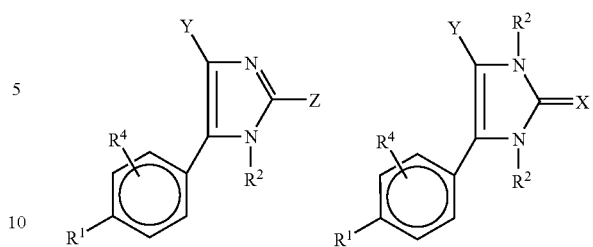

In these compounds, Y is selected from H, $C_1$-$C_4$ alkyl and $C_1$-$C_4$ substituted alkyl, and is preferably H. $R^1$ is selected from H, —OH, halogens (F, Cl, Br and I), $C_1$-$C_4$ alkyl, $C_1$-$C_4$ substituted alkyl, $C_1$-$C_4$ ester, and $C_1$-$C_4$ substituted ester, and is preferably H, —OH, halogen, —$OOCCH_2M$ (where) M is H or a halogen), and is not preferably H. $R^2$ is selected from H, $C_1$-$C_4$ alkyl and $C_1$-$C_4$ substituted alkyl, and it is preferred that at least one of the $R^2$ groups be methyl. $R^3$ is selected from H, $C_1$-$C_4$ alkyl, $C_1$-$C_4$ substituted alkyl, and —$CH_2Ph$; preferred $R^3$ moieties are H and methyl. $R^4$ is selected from H, $C_1$-$C_4$ alkyl and $C_1$-$C_4$ substituted alkyl, and is preferably H. X is selected from S and O, and is preferably S. Finally, the Z moiety is selected from —$SR^3$ and —$OR^3$, and is preferably —$SR^3$. Particularly preferred compounds are those having the structural formulae:

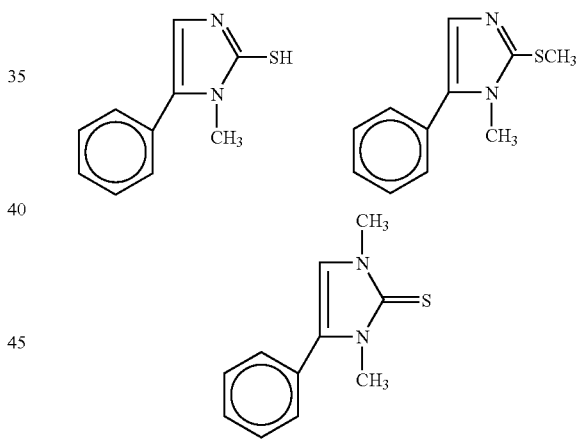

Other preferred compounds include:

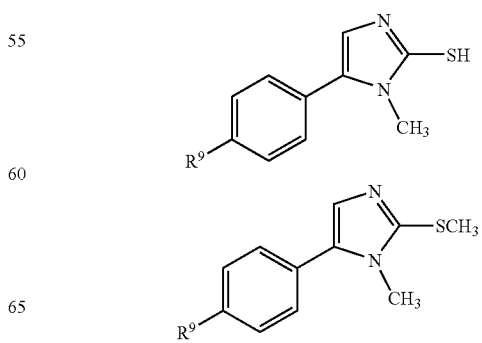

-continued

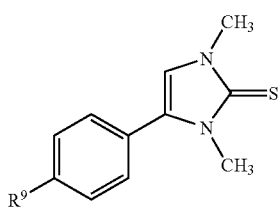

wherein R⁹ is selected from —OH, -M and —OOCCH₂M; and M is selected from F, Cl, Br and I.

Most preferred is the compound having the structure given below.

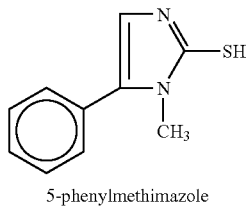

5-phenylmethimazole

Mixtures of the pharmaceutically active compounds defined herein may also be used. The methimazole derivatives and tautomeric cyclic thiones described above can be synthesized using techniques well known to those skilled in the art. For example, the synthesis of several tautomeric cyclic thiones is described in Kjellin and Sandstrom, Acta Chemica Scandanavica 23: 2879-2887 (1969), incorporated herein by reference.

A representative methimazole derivative may be synthesized using the following procedure. Appropriately substituted analogs of acetaldehyde are brominated in the 2-position by treatment with bromine and UV light, followed by formation of the corresponding diethylacetal using absolute ethanol. The bromine is then displaced from this compound by treatment with anhydrous methylamine, or other suitable amine, in a sealed tube at about 120° for up to about 16 hours. Reaction of the resulting aminoacetal with potassium thiocyanate in the presence of hydrochloric acid, at steam bath temperatures overnight, provides the methimazole analogs.

Representative methimazole compounds of the present invention are shown in Table 1.

TABLE 1

| Compounds | | Structure of Compounds. |
|---|---|---|
| | Imidazole | 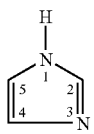 |
| #1 | 1-Methylimidazole-2-thiol (Methimazole) C₄H₆N₂S; 1-Methyl-2-mercapto-imidazole (MMI) | 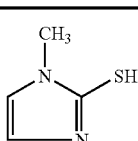 |

TABLE 1-continued

| Compounds | | Structure of Compounds. |
|---|---|---|
| | Imidazole | |
| #2 | 2-Methyl-5-nitro-1-imidazole ethanol (Metronidazole) C₆H₉N₃O₃; MW: 171.16 | |
| #3 | 2-Mercaptoimidazole MW: 100.14 | |
| #4 | 2-Mercaptobenzi-midazole MW: 150.20 | |
| #5 | 2-Mercapto-5-nitro-benzimidazole MW: 195.20 | |
| #6 | 2-Mercapto-5-methyl-benzimidazole MW: 164.23 | |
| #7 | S-Methylmethi-mazole C₅H₈N₂S; MW: 128.20 B.P. 48° @ 100 u (liq.) | |
| #8 | N-Methylmeth-imazole C₅H₈N₂S; MW: 128.20 B.P. 188°-194° | |
| #9 | 5-Methylmeth-imazole C₅H₈N₂S; MW: 128.20 B.P. 254°-255° | |
| #10 | 5-Phenylmeth-imazole C₁₀H₁₀N₂S; MW: 190.27 B.P. 168°-173° | |

TABLE 1-continued

Structure of Compounds.

| Compounds | Imidazole | 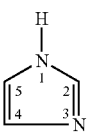 |
|---|---|---|
| #11 | 1-Methyl-2-Thiomethyl-5(4)nitroimidazole | 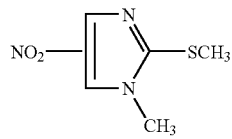 |

The pharmaceutical compositions of the present invention comprise a safe and effective amount of one or more of the methimazole derivatives or tautomeric cyclic thione compounds (i.e., the active compounds). Preferred compositions contain from about 0.01% to about 25% of the active compounds, with most preferred compositions containing from about 0.1% to about 10% of the active compounds. The pharmaceutical compositions of the present invention may be administered in any way conventionally known, for example, intraperitoneally, intravenously, intramuscularly, or topically, although oral administration is preferred. Preferred compositions are in unit dosage form, i.e., pharmaceutical compositions, which are available in a pre-measured form suitable for single dosage administration without requiring that the individual dosage be measured out by the user, for example, pills, tablets or ampules.

The pharmaceutical compositions of the present invention additionally include a pharmaceutically-acceptable carrier compatible with the methimazole derivatives or tautomeric cyclic thiones described above. In addition to the pharmaceutically-acceptable carrier, the pharmaceutical compositions may contain, at their art accepted levels, additional compatible ingredients, such as additional pharmaceutical actives, excipients, formulational aids (e.g., tabletting aids), colorants, flavorants, preservatives, solubilizing or dispersing agents, and other materials well known to those skilled in the art.

As used herein, the term "pharmaceutical carrier" denotes a solid or liquid filler, diluent or encapsulating substance. These materials are well known to those skilled in the pharmaceutical arts. Some examples of the substances which can serve as pharmaceutical carriers are sugars, such as lactose, glucose, and sucrose; starches, such as corn starch and potato starch; cellulose and its derivatives, such as sodium carboxymethyl cellulose, ethyl cellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols, such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. They may comprise liposomes or drug carriers made lipids or polymeric particles, including biodegradable polymers, or targeted delivery applications, e.g., coupling to antibodies. Wetting agents and lubricants, such as sodium lauryl sulfate, as well as coloring agents, flavoring agents, tableting agents, and preservatives, can also be present. Formulation of the components into pharmaceutical compositions is done using conventional techniques.

The pharmaceutical carrier employed in conjunction with the pharmaceutical compositions of the present invention is used at a concentration sufficient to provide a practical size-to-dosage relationship. Preferably, the pharmaceutical carrier comprises from about 25% to about 99.99%, preferably from about 50% to about 99.9%, by weight of the total pharmaceutical composition. The methimazole derivatives or tautomeric cyclic thiones defined in the present application may surprisingly be more soluble than methimazole in conventional carrier materials. This provides significant benefits in allowing greater flexibility in the formulation of pharmaceutical compositions containing methimazole derivatives or tautomeric cyclic thiones, and may allow the use of significantly lower doses of the active compound.

The conditions treated with the pharmaceutical compositions of this invention generally include IBD and the various symptoms that fall within a definition of IBD. The formulations are administered to achieve a therapeutic effect. For those compounds that exhibit a long residency in the body, a once-a-day regimen is possible. Alternatively, multiple doses, such as up to three doses per day, typically, may offer more effective therapy. Thus, a single dose or a multidose regimen may be used.

The present invention also provides for methods of diagnosing and treating ulcerative colitis, which is a disease of the large intestine characterized by chronic diarrhea with cramping abdominal pain, rectal bleeding, and loose discharges of blood, pus and mucus. The manifestations of this disease vary widely. A pattern of exacerbations and remissions typifies the clinical course of most ulcerative colitis patients (70%), although continuous symptoms without remission are present in some patients with ulcerative colitis. Systemic complications of ulcerative colitis include arthritis, eye inflammation such as uveitis, skin ulcers and liver disease. In addition, ulcerative colitis and especially long-standing, extensive disease is associated with an increased risk of colon carcinoma.

Several pathologic features characterize ulcerative colitis in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. Furthermore, the inflammatory process of ulcerative colitis is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerate intestinal crypts are filled with neutrophils, also are typical of the pathology of ulcerative colitis (Rubin and Farber, Pathology (Second Edition) Philadelphia: J.B. Lippincott Company (1994), which is incorporated herein by reference).

In any event, the pharmaceutical composition is administered in such a manner so that compound is delivered into the patient's bloodstream. One excellent mode for accomplishing this is intravenous administration. Intravenous dose levels for treating IBD range from about 0.01 mg/kg/hour of active amide compound to about 100 mg/kg/hour, all for from about 1 to about 120 hours and especially 1 to 96 hours. A preloading bolus of from about 50 to about 5000 mg may also be administered to achieve adequate steady state levels. Other forms of parenteral administration, such as intramuscular or intraperitoneal injection can be used, as well. In this case, similar dose levels are employed.

With oral dosing, one to three oral doses per day, each from about 0.1 to about 150 mg/kg of active compound are employed, with preferred doses being from about 0.15 to about 100 mg/kg. With rectal dosing, one to three rectal doses per day, each from about 1 to about 150 mg/kg of active compound are employed, with preferred doses being from about 1 to about 100 mg/kg.

In any treatment regimen, the health care professional should assess the patient's condition and determine whether or not the patient would benefit from treatment. Some degree of routine dose optimization may be required to determine an optimal doing level and pattern. A positive dose-response relationship has been observed. As such and bearing in mind the severity of the side effects and the advantages of providing maximum possible amelioration of symptoms, it may be desired in some settings to administer large amounts of active compound, such as those described above.

The pharmaceutical compositions of the present invention are administered such that appropriate levels of pharmaceutical active are achieved in the bloodstream. The precise dosage level required in a given case will depend upon, for example, the particular methimazole derivative used, the nature of the disease being treated, and the size, weight, age and physical condition of the patient.

The term "pharmaceutically acceptable salts" refers to salts prepared from pharmaceutically acceptable non-toxic bases or acids including inorganic or organic bases and inorganic or organic acids. Salts derived from inorganic bases include: aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include: salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include: acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. It will be understood that, as used herein, the compounds referred to herein are meant to also include the pharmaceutically acceptable salts.

The magnitude of prophylactic or therapeutic dose of the therapeutic compound of the present invention will, of course, vary with the nature of the severity of the condition to be treated and with the particular therapeutic compound of the present invention and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous or intraperitoneal administration is employed, a suitable dosage range is from about 0.001 mg to about 25 mg (preferably from 0.01 mg to about 1 mg) of a therapeutic compound of the present invention per kg of body weight per day and for cytoprotective use from about 0.1 mg to about 100 mg (preferably from about 1 mg to about 100 mg and more preferably from about 1 mg to about 10 mg) of the therapeutic compound of the present invention per kg of body weight per day.

In the case where an oral composition is employed, a suitable dosage range is, e.g. from about 0.01 mg to about 100 mg of the therapeutic compound of the present invention per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a therapeutic compound of the present invention per kg of body weight per day.

The present invention utilizes pharmaceutical formulation techniques to provide compositions of a methimazole derivatives and tautomeric cyclic thiones for treating the inflammatory diseases of the bowel as hereinbefore defined. The methimazole derivatives and tautomeric cyclic thiones must have a chance to reach the inflamed part of the bowel in sufficient concentration and for a sufficiently long time to exert its local action, in the case of Crohn's disease the whole bowel or only the small intestine and in the case of ulcerative colitis the caecum, colon and the rectum.

In ulcerative colitis, the composition should be formulated so that the methimazole derivatives and tautomeric cyclic thiones are released preferentially during the passage of the colon. In Crohn's disease in the ileum the composition should be formulated so that the methimazole derivatives and tautomeric cyclic thiones are released preferentially during the passage of the small intestine. This can be accomplished by enteric and/or slow release coating of the units containing the methimazole derivatives and tautomeric cyclic thiones.

The dosage and dose rate of the compounds of this invention effective to prevent, suppress or inhibit diseases will depend on a variety of factors, such as the nature of the inhibitor, the size of the patient, the goal of the treatment, the nature of the pathology to be treated, the specific pharmaceutical composition used, and the judgment of the treating physician.

According to another embodiment compositions containing a compound of this invention may also comprise an additional agent selected from the group consisting of: corticosteroids, bronchodilators, anti-asthmatics (mast cell stabilizers), anti-inflammatories, antirheumatics, immunosuppressants, antimetabolites, immunomodulators, antipsoriatics, antibiotics, and antidiabetics. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); and interferons (immunomodulators).

In one embodiment, this aspect additionally involves administering a therapeutic steroid to the patient. By way of non-limiting example, therapeutic steroids may include, for example, glucocorticoids, dexamethasone, prednisone, prednisolone, and betamethasone.

The transit time through the gastro-intestinal canal for different dosage forms are rather well known. When the dosage form has been emptied from the stomach the transit through the small intestine takes 3 to 5 hours. The residence time in the large intestine is considerably longer, 25 to 50 hours. Ideally, for local effects, as long as the dosage form remains in the stomach no release should occur. If colitis in the small intestine is going to be treated the release should continue during about 5 hours after the dosage form has left the stomach. If the large intestine is going to be treated, the local release should ideally start at caecum, and continue for up to 50 hours.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by mixing a compound of the present invention, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders, which may be formulated and the powder composition may be inhaled with the aid of an insufflation powder inhaler device. The preferred delivery systems for inhalation are metered dose inhalation (MDI) aerosol, which may be formulated as a suspension or solution of a compound of the present invention in suitable propellants, such as fluorocarbons or hydrocarbons and dry powder inhalation (DPI) aerosol, which may be formulated as a dry powder of a compound of the present invention with or without additional excipients. Suitable topical formulations include transdermal devices, aerosols, creams, ointments, lotions, dusting powders, and the like.

In practical use, the compounds of the present invention can be combined as the active ingredient in intimate admixture with a pharmaceutical carrier according to conventional pharmaceutical compounding techniques. Because of their ease of administration, tablets and capsules represent the most advantageous oral dosage unit form in which case solid pharmaceutical carriers are obviously employed. If desired, tablets may be coated by standard aqueous or nonaqueous techniques. In addition to the common dosage forms set out above, the therapeutic compound of the present invention may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention, such as methimazole derivatives and tautomeric cyclic thiones. When a compound of the present invention is used contemporaneously with one or more drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VCAM-1 antagonists; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106, 203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, CCR-3, and CXCR4; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) antidiabetic agents such as insulin, sulfonylureas, biguanides (metformin), a-glucosidase inhibitors (acarbose) and glitazones (troglitazone, pioglitazone, englitazone, MCC-555, BRL49653 and the like); (l) preparations of type 1 interferon (e.g., beta-interferon and alpha-interferon); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents; (o) antibiotics; (p) antibodies which block cytokine or chemokine activity, e.g. anti-TNFα, or block leukocyte adhesion, e.g. anti-VCAM-1 or anti-E-selectin.

Combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of ulcerative colitis or inflammatory bowel disorder being treated, the age and condition of the patient, the stage and type of the patient's disease, and how the patient responds to the treatment. Additionally, a person having a greater risk of developing a ulcerative colitis or inflammatory bowel disorder (e.g., a person who is genetically predisposed or previously had a ulcerative colitis or inflammatory bowel disorder) may receive prophylactic treatment to inhibit or delay a response.

The dosage, frequency and mode of administration of each component of the combination can be controlled independently. For example, one compound may be administered orally three times per day, while the second compound may be administered intramuscularly once per day. Combination therapy may be given in on-and-off cycles that include rest periods. The compounds may also be formulated together such that one administration delivers both compounds.

An optionally rate-limiting layer on the compositions comprises a water insoluble polymer or a mixture of water insoluble polymers or a mixture of water soluble and water insoluble polymers.

In one embodiment, the composition comprises the compounds of the present invention and a water-soluble or water-insoluble polymer that acts both as binder for the therapeutic compounds and as a rate-limiting layer for release of the compounds. Such polymers may be selected from cellulose derivatives, acrylic polymers and copolymers, vinyl polymers and other high molecular polymer derivatives or synthetic polymers such as methylcellulose, hydroxypropylcellulose, hydroxypropylmethylcellulose, ethylcellulose, cellulose acetate, polyvinyl pyrrolidone, polyvidone acetate, polyvinyl acetate, polymethacrylates and ethylene-vinyl acetate copolymer or a combination thereof. Preferred film-forming polymers are ethylcellulose or copolymers of acrylic and methacrylic acid esters in aqueous dispersion form.

In another embodiment, the composition comprises homogeneously distributed methimazole derivatives and tautomeric cyclic thiones contained in a water insoluble polymer or a mixture of water insoluble polymers or a mixture of water soluble and water insoluble polymers mentioned above.

In another embodiment, the composition comprises a second rate-limiting layer. The polymers in the second layer may be selected from the group of anionic carboxylic polymers suitable for pharmaceutical purposes and being soluble with difficulty at a low pH but being soluble at a higher pH, the pH limit for solubility being in the interval of pH 4 to pH 7.5, said group comprising cellulose acetate phthalate, cellulose acetate trimellitate, hydroxypropylmethylcellulose phthalate, polyvinyl acetate phthalate and acrylic acid polymers, e.g., partly asterified methacrylic acid-polymers. These polymers may be used alone or in combination with each other or in combination with water insoluble polymers mentioned before.

The coatings may optionally comprise other pharmaceutically acceptable materials that improve the properties of the film-forming polymers such as plasticizers, anti-adhesives, surfactants, and diffusion-accelerating or diffusion-retarding substances. Suitable plasticizers comprise phthalic acid esters, triacetin, dibutylsebacate, monoglycerides, citric acid esters and polyethyleneglycols. Preferred plasticizers are acetyltributyl citrate and triethyl citrate. Suitable anti-adhesives comprise talc and metal stearates.

The amount of the first coating applied on the units is normally in the range between 0.5% and 30% by weight, preferably between 1% and 15%. This amount includes in the relevant case the weight of the steroid as well. The amount of the second coating applied on the units is normally in the range between 1% and 50% by weight, preferably between 2% and 25%, calculated on the weight of the coated units. The remainder constitutes the weight of the dosage.

The weight ratio of the therapeutic compound of the present invention to the second active ingredient may be varied and will depend upon the effective dose of each ingredient. Generally, an effective dose of each will be used. Thus, for example, when a therapeutic is combined with an NSAID the weight ratio of the compound of the therapeutic compound of the present invention to the NSAID will generally range from about 1000:1 to about 1:1000, preferably about 200:1 to about 1:200. Combinations of a therapeutic and other active ingredients will generally also be within the aforementioned range, but in each case, an effective dose of each active ingredient should be used.

The following examples are intended to illustrate the pharmaceutically active compounds, pharmaceutical compositions and methods of treatment of the present invention, but are not intended to be limiting thereof.

EXAMPLES

A causal factor for gastrointestinal damage in ulcerative colitis (UC) is a dysregulated, cytokine-mediated inflammatory response involving leukocytes and specific endothelial cell adhesion molecules (ECAMs). A promising therapeutic approach to suppress UC is to attenuate this aberrant inflammatory process and its immune pathogenesis. Methimazole is used clinically for treatment of autoimmune disease (e.g., Graves' disease). In a recent in vitro study, we found that a derivative of methimazole, phenyl methimazole (C-10), in addition to its anti-immune actions, inhibits tumor necrosis factor-α (TNFα)-induced vascular cell adhesion molecule-1 (VCAM-1) expression and resultant leukocyte-endothelial cell adhesion.

In this study, we used a murine model to determine if C-10 could suppress colitis. C57BL/6J mice were given C-10 (intraperitoneally) coincident with or intermittently during 3% (wt/vol) DSS treatment. Colitis was evaluated by macroscopic colon observation (presence of blood, longitudinal length) and histological analyses of colonic tissue. The mRNA and protein levels of cytokines, chemokines and VCAM-1 in the colon were characterized using Northern blot analyses and immunohistochemistry.

C-10 (i) significantly reversed DSS-induced shortening of the colon; (ii) dramatically suppressed DSS-induced edema, erosion and leukocyte infiltration in colonic mucosa; (iii) inhibited DSS-induced TNFα, interleukin-1β, toll-like receptor-4 (TLR-4), interferon-γ-inducible protein-10 and VCAM-1 mRNA expression and (iv) reduced DSS-induced TLR-4 and VCAM-1 protein expression. C-10 was protective when given coincident with or intermittently during DSS treatment.

These results suggest that C-10 suppresses DSS-induced colitis by inhibiting expression of key inflammatory mediators and leukocyte infiltration, and is a potential therapeutic for colitis.

Materials and Methods

Induction of colitis and treatment with drugs: Male C57BL/6J mice (6 weeks of age, weighing 18-22 gms) were obtained from Jackson Laboratories (Bar Harbor, Me.). Mice were housed in temperature controlled rooms with light-dark cycles. The mice were allowed to adapt to the housing environment for 72 hrs. before starting the experiments. All experiments were carried out in accordance with "Guide for Care and use of Laboratory Animals" (NIH Publication No. 85-23, Revised 1985) and with approval of Ohio University Animal Care and Use Committee. Colitis was induced in a manner similar to that described previously (9). Briefly, mice were given distilled drinking water containing 3% (wt/vol) DSS (MW 30-40 kDa; ICN Biomedicals, Aurora, Ohio) ad libitum (9, 23, 28). As described in individual experiments, mice were given daily intraperitoneal injections of C-10 (Ricerca Inc., Cleveland, Ohio), MMI (Sigma Aldrich, St. Louis, Mo.), Prednisolone (Sigma Aldrich) or C-10 and Prednisolone. Control mice were given daily injections of 2.5% DMSO (Sigma Aldrich; carrier control for C-10) or phosphate buffered saline (PBS; Biofluids, Rockville, Md.; carrier control for MMI and Prednisolone).

Macroscopic Colon Assessment: Mice were killed by cervical dislocation. The whole colon (i.e., including ceacum, proximal colon and distal colon) was excised. The colon was macrosopically assessed by determining (a) the presence or absence of blood in the colon and (b) the longitudinal length of the colon. Subsequently, the whole colon was divided into three parts (i.e., ceacum, proximal colon and distal colon) for histological, Northern blot, and immunohistochemical analyses.

Histological Analysis of Colon: One biopsy of each part of the colon (ceacum, proximal colon and distal colon) was fixed in 4% formalin, dehydrated in serial alcohol, clearanced in chloroform and embedded in paraffin. Sections of 5 µm were stained with Harris's hematoxylin (Fisher Diagnosis, Fisher Scientific Company L.L.C., Middletown, Va.) and eosin and viewed by an investigator blinded to the treatment. Approximately 20 to 25 stained sections of each colon segment (ceacum, proximal and distal colon) were observed from at least 4 different mice in each treatment group. 5 representative sections, approximately 25 µm apart, were histopathologically scored for severity of inflammation (score: 0, none; 1, mild; 2, moderate; and 3, severe), extent of inflammation (score: 0, none; 1, mucosal; 2, mucosal and submucosal; and 3, transmural) and crypt damage (score: 0, none; 1, basal 1/3; 2, basal 2/3; 3, crypts lost but surface epithelium present and 4, crypts and surface epithelium lost). 5 different fields of view were analyzed in each section (28, 29).

RNA isolation and Northern blot analysis: Northern blot analysis was used to characterize the mRNA levels of various factors believed to be involved in the pathogenesis of colitis. Samples of each colon part (ceacum, proximal colon, and distal colon) were washed with PBS and homogenized in Trizol (Invitrogen, Carlsbad, Calif.). The homogenates were either frozen on dry ice then transferred to −70 C storage or RNA was extracted immediately according to the manufacturer's instructions. 20 ug of total RNA was resolved on 1% agarose gels containing 0.66M formaldehyde. RNA was capillary blotted onto Nytran membranes (Schleicher and Schuell Inc., Keene, N.H.), UV cross-linked, and subjected to hybridization. For probes, full length or partial cDNAs were labeled with [α-$^{32}$P] dCTP using the Ladderman Labeling Kit (Takara, Madison, Wis.). Partial or full length cDNAs were obtained as follows: Full length mouse TNFα and mouse TLR4 cDNA were excised from commercially available vectors pORF9-mTNFα and pUNO-mTLR4 (Invivogen, San Diego, Calif.). The G3PDH cDNA was from Clontech (Palo Alto, Calif.). Other probe sequences were synthesized by RT-PCR (30) using the following cDNA specific primers and RNA from either human endothelial cells (hVCAM-1) or mouse macrophages (mIL-1β and mIP-10): human VCAM-1,5'-GACTCCGTCTCATTGACTTGCAGCACCACAG-3 (SEQ ID NO:1) and 5'-ATACTCCCGCATCCT-TCAACTGGGCCTTTCG-3' (SEQ ID NO:2) (1876 bp); mouse IP-10, 5'-CCATCAGCACCATGAACCCAAGTCCT-GCCG-3' (SEQ ID NO:3) and 5'-GGACGTCCTCCT-CATCGTCGACTACACTGG-3' (SEQ ID NO:4) (469 bp); mouse IL-1β, 5'-CTCATCTGGGATCCTCTCCAGC-CAAGCTTC-3' (SEQ ID NO:5) and 5'-CCATGGTTTCT-TGTGACCCTGAGCGACCTG-3' (SEQ ID NO:6) (1006 bp). Northern blots were developed using a Fujifilm FLA 3000. Each experiment was replicated at least twice.

Immunohisochemistry: Immunohistochemistry was used to characterize the protein expression of VCAM-1 and TLR-4. Freshly obtained colon was washed with PBS and frozen in Tissue-Tec OCT (Sakura, Tokyo, Japan). The cryostat sections were fixed in cold acetone, dried, rehydrated with PBS and incubated in PBS containing 10% bovine serum albumin (Sigma Aldrich; for VCAM-1 expression) or mouse serum (collected from C57BL/6J mice; for TLR-4 expression). For characterizing VCAM-1 expression, sections were stained with a rat MAb to mouse VCAM-1 (429MVCAMA; IgG$_{2aκ}$; BD Pharmingen, San Diego, Calif.) for 2 hr. at room temperature (RT). Following the incubation, the sections were washed with PBS and treated with FITC-conjugated anti-rat sera (Zymed Laboratory, San Francisco, Calif.) for 1 hr. at RT. The slides were washed 3 times in PBS, dried and mounted using Gel Mount (Biomeda Comp., Foster City, Calif.). Slides were observed using fluorescent microscopy at 100× ocular and 100× objective using immersion oil for fluorescence (Cargille Laboratories Inc, Cedar Grove, N.J.). For characterizing TLR4 expression, sections were stained with murine biotin-conjugated MAb to human TLR4 (HTA125; IgG2a; IMGENEX, San Diego, Calif.) overnight at 4° C. The next day the sections were washed with PBS, incubated with DAB solution [1 mg/ml DAB (3,3'diamonobencidine, Sigma) and 1.2 µl H$_2$O$_2$ in PBS] for 10 minutes. Following the incubation, the reaction were stopped with distilled water, the sections counterstained with Harris's hematoxylin, dehydrated in ethanol and xylol and mounted in Permount mounting medium (Fisher Diagnosis). The results shown are representative of 10 fields observed along each slide. Each experiment was replicated at least twice.

Statistical Analysis: A single factor ANOVA was used to assess the presence of statistical differences. If ANOVA indicated significant differences between conditions, a Bonferroni test was used for multiple pair-wise comparisons. P values <0.05 were considered statistically significant. Unless stated otherwise, all error bars represent standard deviation.
Results Daily treatment of mice with C-10 does not affect viability. In preliminary experiments, we determined the effect of C-10 on normal mice. Mice were divided into 4 treatment groups (8 mice per group). Group I received daily injections of PBS; group II received daily injections of 2.5% DMSO; group III received daily injections of 5 mg/kg C-10; and group IV received daily injections of 10 mg/kg C-10. In one experiment, the injections were from day 1 to 10 and mice were observed up to day 30. In a separate experiment, the injections were from day 1 to 20 and mice were observed up to day 60. The viability of each group was 100% and there appeared to be no difference in the health of the mice between the 4 groups.

C-10 given coincident with DSS treatment suppresses DSS induced colitis. VCAM-1 has been shown to play a role in DSS induced colitis in a murine model (9). This fact, combined with our recent finding that C-10 inhibits TNFα induced VCAM-1 expression on cultured endothelial cells (22), led us to investigate the effect of C-10 in a murine model of DSS induced colitis.

Initially, we probed the effects of C-10 given coincident with DSS treatment. Mice were divided into 4 treatment groups (8 mice per group). Group AN were normal mice that did not receive DSS and were given daily injections of PBS; Group AC1 received DSS; group AC2 received DSS and daily injections of 2.5% DMSO [Both of these groups (AC1, AC2) were DSS-treatment controls—in these and subsequent experiments there was no difference between these two DSS treatment groups.]; Group AE, the experimental treatment group, received DSS and daily injections of 5 mg/kg C-10 in 2.5% DMSO. The C-10, DMSO and PBS treatments were started on the same day as DDS was added to the water.

The mice were sacrificed on day 7 and macroscopic and microscopic histological analysis of the colon was performed (28, 29, 31). This analysis revealed that treatment with C-10 significantly inhibited DSS induced colitis. Specifically, daily administration of 5 mg/kg C-10 coincident with DSS treatment significantly reversed the DSS induced shortening of the colon (AE vs. AC1 and AC2), i.e., the average colon length of DSS treated mice given C-10 was visibly significantly greater than the average colon length of DSS treated mice (AE vs. AC1 and AC2). Note, DMSO (carrier control for C-10) had no effect on DSS induced shortening of the colon (AC2 vs. AC1). Macroscopic observations revealed the consistent presence of blood throughout the colon of DSS treated mice, but rarely, if ever, in the colon of normal mice (AN vs. AC1). The appearance of blood was less frequent (especially in the proximal and distal colon) in 5 mg/kg C-10 treated DSS mice (AE vs. AC1) but not in DMSO treated DSS mice (AC2 vs. AC1). Similar results were observed for mice treated with 10 mg/kg C-10.

Histological analysis of the colons from the various treatment groups was performed and scored as described in the Materials and Methods section. Representative images were evaluated as described below Table 2 and scores are presented in Table 2. (Note, there was no difference between DSS mice+/−DMSO in Table 2) Tissue sections from normal (AN) mice revealed no histological abnormalities (Table 2). In contrast, tissue sections from DSS mice (AC1) revealed severe inflammation that was characterized by the presence of edema and infiltration of inflammatory cells (Table 2). Extensive damage resulting in loss of mucosal structure and crypt destruction was also observed in DSS treated mice (Table 2). Consequently, the histological score of DSS treated mice was greatly increased relative to control mice (Table 2). Tissue sections from 5 mg/kg C-10-treated DSS mice (AE) revealed significant attenuation in inflammation that was characterized by a reduction in infiltration of inflammatory cells and dramatic suppression of edema (Table 2). C-10 administration was also effective in protecting against DSS induced crypt damage (Table 2). Consequently, the histological score of C-10 treated DSS mice was greatly reduced compared to DMSO treated DSS mice (Table 2). Similar results were observed for mice treated with 10 mg/kg C-10.

TABLE 2

| Group | Inflammation Severity | Inflammation Extent | Crypt Damage | Total |
|---|---|---|---|---|
| Normal (AN) | 0 | 0 | 0 | 0 |
| DSS (AC1) | 3.0 ± 0.2 | 2.7 ± 0.3 | 3.6 ± 0.2 | 9.3 ± 0.5 |
| DSS + DMSO (AC2) | 3.1 ± 0.3 | 2.5 ± 0.2 | 3.8 ± 0.2 | 9.4 ± 0.6 |
| DSS + 5 mg/kg C10 (AE) | 0.5 ± 0.2 | 0.7 ± 0.3 | 1.2 ± 0.2 | 2.4 ± 0.7 |

In Table 2, C-10 given coincident with DSS treatment significantly reverses DSS induced histological abnormalities. Histological analyses of the distal colons from various treatment groups were performed. The stained sections were scored (by an investigator blinded to the treatment) for severity of inflammation (score: 0, none; 1, mild; 2, moderate; and 3, severe), extent of inflammation (score: 0, none; 1, mucosal; 2, mucosal and submucosal; and 3, transmural) and crypt damage (score: 0, none; 1, basal 1/3; 2, basal 2/3; 3, crypts lost but surface epithelium present and 4, crypts and surface epithelium lost). 5 different sections, approximately 25 µm apart, were analyzed from at least 4 different mice in each treatment group. Each section was analyzed in 5 different fields of view. The scores presented are average+/−SE. Values from three experiments in duplicate. Bold values represent significant inhibition (P<0.05 or better).

Taken together, the results presented in this section clearly demonstrate that C-10 given coincident with DSS treatment suppresses DSS induced colitis.

C-10 given intermittently during DSS treatment protects against DSS induced colitis Having established that coincident C-10-treatment suppresses DSS induced colitis (Table 2), we proceeded to investigate the protective effects of C-10 when administered intermittently during DSS treatment or after DSS treatment was initiated. In addition, we compared the effects of C-10 to the effect of MMI (which has been shown to be effective in a rat model of colitis (20)) and prednisolone (a standard drug used in treatment of colitis (32) on DSS induced colitis.

Mice were divided into 8 treatment groups (6 mice per group). Group BN did not receive DSS and were given daily injections of PBS; Group BC, the disease control, received DSS; Group BE1 received DSS and daily injections of 5 mg/kg C-10 after DSS treatment was initiated, i.e. from day 2 to day 6; Group BE2 received DSS and daily injections of 5 mg/kg C-10 from day 1 to day 6; Group BE3 received DSS and daily injections of 5 mg/kg C-10 after DSS treatment was initiated, i.e. from day 5 to day 10; Group BE4 received DSS and daily injections of 25 mg/kg MMI from day 1 to day 10 (see 14); Group BE5 received DSS and daily injections of 5 mg/kg prednisolone from day 1 to day 10; and group BE6 received DSS and daily injections of 5 mg/kg C-10 and 5 mg/kg prednisolone daily from day 1 to day 10. The mice were sacrificed on day 10 and macroscopic and microscopic histological analysis of the colon was performed (28, 29, 31).

Macroscopic colon observations revealed that the colon length of DSS treated mice was significantly shorter compared to the colon length of the normal mice (BC vs. BN). C-10 given from days 2 to 6, days 1 to 6 or days 5 to 10 significantly, reversed the DSS induced shortening of colon length (BE1, BE2 and BE3 vs. BC). Thus, the average colon length of DSS treated mice given C-10 from days 2 to 6, days 1 to 6 or days 5 to 10 was significantly greater than the average colon length of DSS treated mice (BE1, BE2 and BE3 vs. BC). Moreover, the average colon length of DSS treated mice given C-10 from days 5 to 10 was not significantly different from control mice (BE3 vs. BC). Coincident MMI administration from day 1 to day 10 significantly reversed the DSS induced shortening of colon length (BE4 vs. BC). C-10 appeared to be as effective as MMI and prednisolone (e.g. BE3 vs. BE4 and BE5). In sum, based on colon length alone, C-10 given for 5 days after DSS treatment was initiated appeared to be as effective as MMI and prednisolone given throughout the DSS treatment (e.g. BE3 vs. BE4 and BE5). Treatment with C-10 and prednisolone in combination (BE6) did not appear to have a beneficial effect compared to treatment with C-10 (BE3) or prednisolone (BE5) alone.

Macroscopic observations revealed the consistent presence of blood throughout the colon of DSS treated mice, but rarely, if ever, in the colon of normal mice (BC vs. BN). The appearance of blood was less frequent (especially in proximal and distal colon) in C-10 treated DSS mice (BE1, BE2, BE3 vs. BC), MMI treated DSS mice (BE4 vs. BC), prednisolone treated DSS mice (BE5 vs. BC) and C-10/prednisolone treated DSS mice (BE6 vs. BC). The group treated with C-10 for 5 days, after DSS treatment had already proceeded for 5 days (BE3), was the only group which like normals (BN) had no blood in any portion of the colon.

Histological analysis of the distal colons from the treatment groups was again performed and scored as described in the Materials and Methods section. Representative images were used to score changes and scores for the entire group are presented in Table 3. Tissue sections from normal mice revealed no histological abnormalities (Table 3, BN). In contrast, tissue sections from DSS mice revealed severe inflammation that was characterized by the presence of edema and infiltration of inflammatory cells (Table 3, BC). Extensive damage resulting in loss of mucosal structure and crypt destruction was also observed in DSS treated mice (Table 3, BC). Consequently, the histological score of DSS treated mice was greatly increased relative to control (Table 3) as noted in the first experiment (Table 2). Tissue sections of DSS mice treated with C-10 from days 5 to 10 (BE3) revealed significant attenuation in inflammatory cellular infiltrate, dramatic suppression of edema and reduction in mucosal damage (Table 3, BE3). Similar reduction in inflammation was observed in BE2 and to a lesser extent in BE1 (data not shown). Although MMI appeared to reduce inflammation and crypt damage, the recovery did not appear to be as significant as C-10 treatment (Table 3; BE4 vs. BE3). The effect of C-10 on reducing inflammation and crypt damage appeared to be similar to that of prednisolone (Table 3, BE3 vs. BE5) and a combination of C-10 and prednisolone was similar to treatment with either compound alone (BE6 vs. BE3 and BE5).

TABLE 3

| Group | Inflammation Severity | Inflammation Extent | Crypt Damage | Total |
|---|---|---|---|---|
| Normal (BN) | 0 | 0 | 0 | 0 |
| DSS (BC) | 3.2 ± 0.3 | 2.6 ± 0.3 | 3.6 ± 0.3 | 9.4 ± 0.5 |
| DSS + 5 mg/kg C10 (BE3) | 0.8 ± 0.2 | 0.7 ± 0.3 | 1.4 ± 0.2 | 2.9 ± 0.7 |
| DSS + 25 mg/kg MMI (BE4) | 2.3 ± 0.4 | 2.1 ± 0.3 | 2.9 ± 0.4 | 7.3 ± 0.3 |
| DSS + 5 mg/kg Prednisolone | 0.9 ± 0.3 | 1.3 ± 0.3 | 1.7 ± 0.2 | 3.9 ± 0.8 |

Table 3. C-10 given intermittently during DSS treatment significantly reverses DSS induced histological abnormalities. Histological analysis of the distal colons from various treatment groups was performed. The stained sections were scored (by an investigator blinded to the treatment) for severity of inflammation (score: 0, none; 1, mild; 2, moderate; and 3, severe), extent of inflammation (score: 0, none; 1, mucosal; 2, mucosal and submucosal; and 3, transmural) and crypt damage (score: 0, none; 1, basal 1/3; 2, basal 2/3; 3, crypts lost but surface epithelium present and 4, crypts and surface epithelium lost). 5 different sections, approximately 25 µm apart, were analyzed from at least 4 different mice in each treatment group. Each section was analyzed in 5 different fields of view. The scores presented are average+/−SE.

Combined, the results presented in this section demonstrate that C-10, given intermittently during DSS treatment, and even 5 days after DSS treatment, protects against DSS induced colitis. Importantly, the results suggest that C-10 is more effective than MMI at protecting against DSS induced colitis and equally effective as prednisolone.

C-10 given after DSS treatment is initiated improves survival and protects against DSS induced colitis by comparison to identical treatment with MMI or prednisolone Preliminary experiments revealed that mice begin to die after extended (>10 days) treatment with DSS (data not shown). Given the efficacy of C-10 in reducing inflammation after DSS treatment had started (Group BE3 above), we next probed the ability of C-10 to increase survival. Mice were given DSS from day 1 to 14. From day 5 to day 10, groups of mice (8 mice per group) were treated with either DMSO, C-10 (5 mg/kg), MMI (25 mg/kg) or prednisolone (5 mg/kg). At day 10, the extent of rectal bleeding was determined and at day 14 the % of mice that survived in each group was determined. C-10 appeared to be significantly more efficacious in preventing rectal bleeding than MMI or prednisolone alone. More importantly, C-10 greatly enhanced survival as compared to mice treated with DMSO alone, MMI alone or prednisolone alone.

C-10 inhibits DSS-increased TNFα, IL-1β, IP-10, TLR4 and VCAM-1 expression. Although the initiating and sequence of propagating events that lead to and sustain colitis have not been fully elucidated, it is fairly clear that bacterial infection and TLR4, cytokines, chemokines, and ECAMs play a key role (4, 20, 32-35). Thus, we investigated the effect of C-10 on expression of TNFα, IL-β (pro-inflammatory cytokines), IP-1β [a representative chemokine known to play a role in colitis (3)], VCAM-1 [an ECAM known to play a role in colitis (9)] and TLR-4 [a receptor for gram-negative bacterial lipopolysaccharide endotoxins implicated in colitis (2)].

Northern blot analysis revealed that the colon of normal mice did not express TNFα or IL-1β mRNA (BN). In contrast mice treated with DSS (BC) or DSS plus DMSO (data not shown) expressed significant TNFα and IL-1β mRNA primarily in the distal colon (BC). C-10 given in various dose regimes clearly inhibited DSS-induced TNFα and IL-1β mRNA expression in the distal colon (BE1, BE2, and BE3 vs. BC). Interestingly, the C-10 dose regime that was the most effective at reversing DSS-induced shortening of colon, rectal bleeding, and histologic inflammation (BE3) had the greatest inhibitory effect on TNFα and IL-1β mRNA expression. Prednisolone and a combination of C-10 and prednisolone also reduced TNFα and IL-1β mRNA expression (BE5, BE6 vs. BC); MMI was effective but slightly less so for IL-1β (BE4 vs. BC and BE3). Similar results were obtained for mRNA expression of IP-10. Specifically, DSS-induced IP-10 expression was predominantly observed in the distal colon (AC1 and BC) and was inhibited by C-10, MMI, prednisolone and a combination of C-10 and prednisolone (AE and BE3, BE4, BE5, BE6).

Northern blot analysis revealed that the colon of normal mice expressed a low level of TLR-4 mRNA (BN) primarily in the proximal and distal colon. Mice treated with DSS expressed increased levels of TLR-4 mRNA (BC). C-10 given in various dose regimes appeared to inhibit DSS-induced increased TLR-4 mRNA expression (BE1, BE2, BE3 vs. BC). Prednisolone appeared to inhibit TLR-4 mRNA expression while the effect of MMI was unclear (BE5, BE4 vs. BC). Immunohistochemical analysis confirmed that C-10 had a distinct inhibitory effect on TLR-4 protein expression as determined by far fewer intestinal epithelial cells with TLR4 overexpressed, less intense staining of the intestinal epithelial cells, and reversion to levels in normal intestinal epithelial cells.

Northern blot analysis revealed that the colon of normal mice did not express VCAM-1 mRNA (AN). Mice treated with DSS expressed significant levels of VCAM-1 mRNA (AC1) and protein measured in situ by immunofluorescence. C-10 diminished VCAM-1 mRNA expression (AE) and this decrease was paralleled at the protein level measured in situ by immunofluorescence.

Discussion

Key aspects of colitis are edema, leukocyte recruitment, and infiltration of the tissue (1). This is characterized by an increased expression of pro-inflammatory cytokines (e.g. TNFα), ECAMs (e.g., VCAM-1), and chemokines (e.g., IP-10) (1, 3, 4, 9). Several therapeutic approaches seek to diminish colitis by inhibiting the increased expression of these molecules involved in the inflammatory response. Previously, we have demonstrated that C-10 inhibits TNFα induced VCAM-1 expression in human arterial cells and consequent leukocyte adhesion (22). In this paper we probed the hypothesis that C-10 could act in vivo to diminish DSS-induced colitis through a process that involves suppression of VCAM-1, a key mediator of inflammation. We show that C-10 is effective in colitis and provide evidence that its action involves not only an effect on VCAM-1 but also appears to act as a broad anti-inflammatory as well as anti-immune agent.

Our results clearly demonstrate that C-10 can significantly inhibit DSS-induced colitis. Specifically, C-10 attenuated DSS-induced shortening of the colon and attenuated the presence of blood in the colon. These macroscopic observations paralleled the microscopic histological analysis. In particular, C-10 dramatically suppressed edema, reduced leukocyte infiltration and maintained mucosal integrity. Remarkably, we observed that C-10 suppressed DSS-induced mucosal inflammation along the entire length of the colon (i.e. caecum to distal colon). These data are likely broadly applicable to other colitis models and human colitis since the macroscopic and microscopic manifestations of colitis observed in our system have been reported in other animal models of colitis as well as in humans (36).

We anticipated C-10 might be effective in colitis since we have previously shown that C-10 inhibits TNFα induced VCAM-1 expression (22). Surprisingly, our study revealed that, in addition to decreasing VCAM-1 expression, C-10 diminished DSS-induced expression of important inflammatory mediators: IL-1β, TNFα, IP-10, and TLR-4. The importance of TLR-4 has recently been shown in humans and in a separate animal model of colitis. Thus, recent work indicated that TLR-4, which recognizes gram-negative bacterial lipopolysaccharide, was strongly up-regulated in both CD and UC (2). This observation is related to studies of the myeloid cell-specific Stat3-deficient mouse, which is one of several experimentally induced models of enterocolitis used to understand the mechanism of development of human inflammatory bowel disease such as CD and UC (4). This model, which exhibits severe Th1-mediated enterocolitis, is significantly improved in TLR-4/Stat3-deficient mice, whereas TNFα/Stat3 deficient mice still had severe enterocolitis, indicating the importance of innate immunity and TLR-4 in Th1-dependent enterocolitis (4). Kobayashi et al. (4) proposed that resident microflora in a damaged colon may be able to overstimulate TLR-4 signaling under certain genetic conditions, resulting in overproduction of inflammatory cytokines (e.g., TNFα). TLR-4 signals its effects through two adapter molecules: MyD88, which activates NF-κB, MAPK, and various cytokines, and the TIR domain-containing molecule adapter inducing IFN-β/TIR-containing adapter molecule (TRIF/TICAM)-1, which activates IFN regulatory factor (IRF)-3 and causes the synthesis and release of type I IFNs (α or β) (24-27). It would appear, therefore, that C-10, by diminishing TLR-4-mediated signaling, might attenuate expression of pro-inflammatory cytokines (e.g., TNFα) and chemokines (e.g., IP-10). Together with the consequent decrease in VCAM-1, C-10 could block leukocyte infiltration and consequent tissue damage. While this scenario is somewhat speculative, it is consistent with the data generated to date and suggests C-10 acts to suppress several causative factors in colitis, not only VCAM-1 and abnormal leukocyte adhesion.

MMI has been shown to be broadly active in several autoimmune diseases (12-18). Among its actions was suppression of immune markers such as major histocompatibility complex (MHC) Class 1 and 2. C-10 was developed as a more potent immunosuppressive based on its ability to improve suppression of IFN-induced MHC gene expression (18) The finding that C-10 has a potential effect on innate immunity and inflammation thus extends its usefulness and appears to make it a potentially good agent in UC and inflammatory bowel disease since its action is more broad and more effective than MMI. The data suggesting that C-10 is better than prednisolone may not be surprising, since prednisolone is a steroid that suppresses the immune inflammatory response but is not known to attack its root causes. The data on survival and rectal bleeding is a telling head to head comparison.

Macrophages/monocytes are activated by intracellular parasites and/or endotoxin or other bacterial or viral disease trough the IL1-like receptor (IL-1-R), Toll Like Receptor 4, and secrete pro-inflammatory TNFα, IL-12, IL-1β and IL-6. (37). Excessive and uncontrolled secretion of these cytokines result in serious local and systemic inflammatory process leading to serious local and systemic complications such as microcirculatory dysfunction, tissue damage and septic shock with high mortality.

Activated T lymphocytes, CD4+, secrete TNFα, which leads to a Th1 immune response and associated pathologies. The cytokines present when naïve T cells are first activated greatly influence whether the response will be polarized toward Th1 or Th2 differentiation. (38). The primary molecules associated with Th1 differentiation from naïve T cells are IL-12 and TNFα (38). Activated Th1 cells release IFNγ and TNFα, which are potent stimulator of cell-mediated effector mechanisms. These mechanisms are responsible of many disease associated with Th1 cytokines. Thus, TNFα has been described as one of the more important cytokines that are released by the activation of CD4+, Th1 lymphocytes and cause the Th1 dependent cytokine diseases (38, 39).

In this context, blocking TNFα and IL-1 secretion is a good therapeutic strategy such that it should block the effect of the pro-inflammatory and Th1 cytokines. Th1 cytokine-dependent inflammatory diseases, associated with the TNFα cytokine activity, according to a recent review by Szabo S. J et al. 2003 (39), include Crohn's and inflammatory bowel diseases in rodent modes. Multiple sclerosis, diabetes, autoimmune thyroid disease and lupus are other diseases in this group (39). The same authors and Rich R. et. al. 2001 (38) showed that Th1 cells are responsible of organ damage in various organ-specific autoimmune disease and other immunological diseases: Hashimoto's thyroiditis, rheumatoid arthritis, multiple sclerosis, rheumatic heart diseases, autoimmune hepatitis, Guillain Barre, autoimmune peripheral neuropathies, celiac sprue, ulcerative colitis, Crohn's disease, Myocarditis, Goodpasture's disease, primary biliary cirrosis, autoimmune hepatitis, myasthenia gravis, type I diabetes, pemfigus and other bullous diseases, orchitis and oophoritis, sarcoidosis, uveitis, scleritis, keratitis, corneal transplant rejection, and solid organ transplantation.

In conclusion, we have demonstrated that phenyl methimazole (C-10) suppresses DSS-induced murine colitis through a process that involves inhibition of a broad array of key mediators of inflammation in addition to VCAM-1. C-10 is protective both when given coincident with, intermittently during, and, importantly, after DSS treatment has started, i.e. a situation akin to the natural course of treatment for inflammatory bowel disease. Thus, C-10 may be a potential therapeutic for inflammatory bowel diseases such as ulcerative colitis.

Pharmaceutical Compositions of the Present Invention

For the treatment of cell adhesion and inflammation disorders, pharmaceutical compositions in dosage unit form comprise an amount of composition which provides from about 0.05 to about 60 milligrams, preferably from about 0.05 to about 20 milligrams, of active compound per day. Useful pharmaceutical formulations for administration of the active compounds of this invention may be illustrated below. They are made using conventional techniques.

| CAPSULES | |
|---|---|
| Active ingredient | 0.05 to 20 mg |
| Lactose | 20-100 mg |
| Corn Starch U.S.P. | 20-100 mg |
| Aerosolized silica gel | 2-4 mg |
| Magnesium stearate | 1-2 mg |
| TABLETS | |
| Active ingredient | 0.05 to 20 mg |
| Microcrystalline cellulose | 50 mg |
| Corn Starch U.S.P. | 80 mg |
| Lactose U.S.P. | 50 mg |
| Magnesium stearate U.S.P. | 1-2 mg |

This tablet can be sugar coated according to conventional art practices. Colors may be added to the coating.

| CHEWABLE TABLETS | |
|---|---|
| Active ingredient | 0.05 to 20 mg |
| Mannitol, N.F. | 100 mg |
| Flavor | 1 mg |
| Magnesium stearate U.S.P. | 2 mg |
| SUPPOSITORIES | |
| Active ingredient | 0.05 to 20 mg |
| Suppository base | 1900 mg |
| Dimethyl sulfoxide | 0.1 to 3% |
| LIQUID | |
| Active ingredient | 2.0 percent |
| Polyethylene glycol 300, N.F. | 10.0 percent |
| Glycerin | 5.0 percent |
| Sodium bisulfite | 0.02 percent |
| Sorbitol solution 70%, U.S.P. | 50 percent |
| Methylparaben, U.S.P. | 0.1 percent |
| Propylparaben, U.S.P. | 0.2 percent |
| Distilled water, U.S.P. (q.s.) | 100.0 cc |
| Dimethyl sulfoxide | 0.1 to 3% |
| INJECTABLE | |
| Active ingredient | 0.05 to 60 mg |
| Polyethylene glycol 600 | 1.0 cc |
| Sodium bisulfite, U.S.P. | 0.4 mg |
| Water for injection, U.S.P. (q.s.) | 2.0 cc |
| Dimethyl sulfoxide | 0.1 to 3% |

In addition, information regarding procedural or other details supplementary to those set forth herein is described in cited references specifically incorporated herein by reference.

It would be obvious to those skilled in the art that modifications or variations may be made to the preferred embodiment described herein without departing from the novel teachings of the present invention. All such modifications and variations are intended to be incorporated herein and within the scope of the claims.

REFERENCES

1. Grisham, M. B., and D. N. Granger. 1999. Leukocyte-endothelial cell interactions in inflammatory bowel disease. In *Inflammatory bowel disease*. J. B. Kirsner, ed. Saunders, Philadelphia, p. 55-64.
2. Cario, E., and D. K. Podolsky. 2000. Differential alteration in intestinal epithelial cell expression of toll-like receptor 3 (TLR3) and TLR4 in inflammatory bowel disease. *Infect Immun* 68:7010-7017.
3. Singh, U. P., S. Singh, D. D. Taub, and J. W. Lillard, Jr. 2003. Inhibition of IFN-gamma-inducible protein-10 abrogates colitis in IL-10-/- mice. *J Immunol* 171:1401-1406.
4. Kobayashi M, Kweon M N, Kuwata H et al. Toll-like receptor-dependent production of IL-12p40 causes chronic enterocolitis in myeloid cell-specific Stat3-deficient mice. *J Clin Invest* 2003; 111(9):1297-308.
5. Carlos, T. M., and J. M. Harlan. 1994. Leukocyte-endothelial adhesion molecules. *Blood* 84:2068-2101.
6. Luscinskas, F. W., and M. A. Gimbrone. 1996. Endothelial-dependent mechanisms in chronic inflammatory leukocyte recruitment. *Annu. Rev. Med.* 47:413-421.

7. Springer, T. A. 1994. Traffic signals for lymphocyte recirculation and leukocyte emigration: the multistep paradigm. *Cell* 76:301-314.
8. Targan, S. R., S. B. Hanauer, S. J. van Deventer, L. Mayer, D. H. Present, T. Braakman, K. L. DeWoody, T. F. Schaible, and P. J. Rutgeerts. 1997. A short-term study of chimeric monoclonal antibody cA2 to tumor necrosis factor alpha for Crohn's disease. Crohn's Disease cA2 Study Group. *N Engl J Med* 337:1029-1035.
9. Soriano, A., A. Salas, M. Sans, M. Gironella, M. Elena, D. C. Anderson, J. M. Pique, and J. Panes. 2000. VCAM-1, but not ICAM-1 or MAdCAM-1, immunoblockade ameliorates DSS-induced colitis in mice. *Lab. Invest.* 80:1541-1551.
10. Wallace, J. L., A. Higa, G. W. McKnight, and D. E. MacIntyre. 1992. Prevention and reversal of experimental colitis by a monoclonal antibody which inhibits leukocyte adherence. *Inflammation* 16:343-354.
11. Conner, E. M., S. Brand, J. M. Davis, F. S. Laroux, V. J. Palombella, J. W. Fuseler, D. Y. Kang, R. E. Wolf, and M. B. Grisham. 1997. Proteasome inhibition attenuates nitric oxide synthase expression, VCAM-1 transcription and the development of chronic colitis. *J Pharmacol Exp Ther* 282:1615-1622.
12. Cooper, D. S. 1984. Antithyroid drugs. *N Engl J Med* 311:1353-1362.
13. Elias, A. N., R. J. Barr, M. K. Rohan, and K. Dangaran. 1995. Effect of orally administered antithyroid thioureylenes on PCNA and P53 expression in psoriatic lesions. *Int J Dermatol* 34:280-283.
14. Singer, D. S., L. D. Kohn, H. Zinger, and E. Mozes. 1994. Methimazole prevents induction of experimental systemic lupus erythematosus in mice. *J Immunol* 153:873-880.
15. Chan, C. C., I. Gery, L. D. Kohn, R. B. Nussenblatt, E. Mozes, and D. S. Singer. 1995. Periocular inflammation in mice with experimental systemic lupus erythematosus. A new experimental blepharitis and its modulation. *J Immunol* 154:4830-4835.
16. Davies, T. F., I. Weiss, and M. A. Gerber. 1984. Influence of methimazole on murine thyroiditis. Evidence for immunosuppression in vivo. *J Clin Invest* 73:397-404.
17. Wang, P., S. H. Sun, P. B. Silver, C. C. Chan, R. K. Agarwal, B. Wiggert, L. D. Kohn, G. A. Jamieson, Jr., and R. R. Caspi. 2003. Methimazole protects from experimental autoimmune uveitis (EAU) by inhibiting antigen presenting cell function and reducing antigen priming. *J Leukoc Biol* 73:57-64.
18. Kohn, L. D., R. W. J. Curley, and J. M. Rice. 2002. Methimazole derivatives and tautomeric cyclic thiones to treat autoimmune diseases. U.S. Pat. No. 6,365,616.
19. Wenisch, C., D. Myskiw, A. Gessl, and W. Graninger. 1995. Circulating selectins, intercellular adhesion molecule-1, and vascular cell adhesion molecule-1 in hyperthyroidism. *J Clin Endocrinol Metab* 80:2122-2126.
20. Oren, R., Y. Maaravi, F. Karmeli, G. Kenet, L. Zeidel, A. Hubert, and R. Eliakim. 1997. Anti-thyroid drugs decrease mucosal damage in a rat model of experimental colitis. *Aliment Pharmacol Ther* 11:341-345.
21. Singer, D. S., L. D. Kohn, E. Mozes, M. Saji, J. Weissman, G. Napolitano, and F. D. Ledley. 1996. Methods for assessing the ability of a candidate drug to suppress MHC class I expression. U.S. Pat. No. 5,556,754.
22. Dagia, N. M., N. Harii, A. E. Meli, X. Sun, C. J. Lewis, L. D. Kohn, and D. J. Goetz. 2004. Phenyl methimazole inhibits TNFα-induced VCAM-1 expression in an IFN Regulatory Factor-1-dependent manner and reduces monocytic cell adhesion to endothelial cells-*J Immunol* 173:2041-2049.
23. Lange, S., D. S. Delbro, E. Jennische, and I. Mattsby-Baltzer. 1996. The role of the Lps gene in experimental ulcerative colitis in mice. *Apmis* 104:823-833.
24. Takeda, K., and S. Akira. 2003. Toll receptors and pathogen resistance. *Cell Microbiol* 5:143-153.
25. Takeda, K., T. Kaisho, and S. Akira. 2003. Toll-like receptors. *Annu Rev Immunol* 21:335-376.
26. Oshiumi, H., M. Matsumoto, K. Funami, T. Akazawa, and T. Seya. 2003. TICAM-1, an adaptor molecule that participates in Toll-like receptor 3-mediated interferon-beta induction. *Nat Immunol* 4:161-167.
27. Yamamoto, M., S. Sato, K. Mori, K. Hoshino, O. Takeuchi, K. Takeda, and S. Akira. 2002. Cutting edge: a novel Toll/IL-1 receptor domain-containing adapter that preferentially activates the IFN-beta promoter in the Toll-like receptor signaling. *J Immunol* 169:6668-6672
28. Bendjelloul, F., P. Rossmann, P. Maly, V. Mandys, M. Jirkovska, L. Prokesova, L. Tuckova, and H. Tlaskalova-Hogenova. 2000. Detection of ICAM-1 in experimentally induced colitis of ICAM-1-deficient and wild-type mice: an immunohistochemical study. *Histochem J* 32:703-709.
29. Mabley, J. G., P. Pacher, L. Liaudet, F. G. Soriano, G. Hasko, A. Marton, C. Szabo, and A. L. Salzman. 2003. Inosine reduces inflammation and improves survival in a murine model of colitis. *Am J Physiol Gastrointest Liver Physiol* 284:G138-144.
30. Suzuki, K., A. Mori, K. J. Ishii, J. Saito, D. S. Singer, D. M. Klinman, P. R. Krause, and L. D. Kohn. 1999. Activation of target-tissue immune-recognition molecules by double-stranded polynucleotides. *Proc Natl Acad Sci USA* 96:2285-2290.
31. Dieleman, L. A., M. J. Palmen, H. Akol, E. Bloemena, A. S. Pena, S. G. Meuwissen, and E. P. Van Rees. 1998. Chronic experimental colitis induced by dextran sulphate sodium (DSS) is characterized by Th1 and Th2 cytokines. *Clin Exp Immunol* 114:385-391.
32. Tuvlin, J. A., and S. V. Kane. 2003. Novel therapies in the treatment of ulcerative colitis. *Expert Opin Investig Drugs* 12:483-490.
33. Pallone, F., V. Blanco Gdel, P. Vavassori, I. Monteleone, D. Fina, and G. Monteleone. 2003. Genetic and pathogenetic insights into inflammatory bowel disease. *Curr Gastroenterol Rep* 5:487-492.
34. Panes, J., and D. N. Granger. 1998. Leukocyte-endothelial cell interactions: molecular mechanisms and implications in gastrointestinal disease. *Gastroenterology* 114:1066-1090.
35. Ortega-Cava, C. F., S. Ishihara, M. A. Rumi, K. Kawashima, N. Ishimura, H. Kazumori, J. Udagawa, Y. Kadowaki, and Y. Kinoshita. 2003. Strategic compartmentalization of Toll-like receptor 4 in the mouse gut. *J Immunol* 170:3977-3985.
36. Fiocchi, C. 1998. Inflammatory bowel disease: etiology and pathogenesis. *Gastroenterology* 115:182-205.

What is claimed is:

1. A method for the amelioration of episodes of acute or chronic ulcerative colitis in a mammal comprising administering to the mammal a pharmaceutical composition comprising an active compound having the formula selected from the group consisting of:

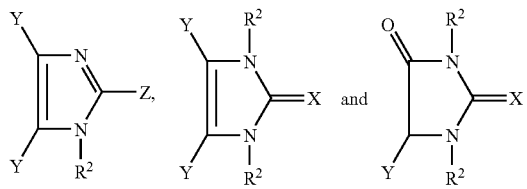

wherein Y is selected from the group consisting of H, $C_1$-$C_4$ alkyl, $C_1$-$C_4$ substituted alkyl, —$NO_2$, and the phenyl moiety:

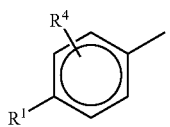

and wherein no more than one Y group in said active compound is the phenyl moiety; $R^1$ is selected from the group consisting of H, —OH, $C_1$-$C_4$ alkyl, and $C_1$-$C_4$ substituted alkyl; $R^2$ is selected from the group consisting of H, $C_1$-$C_4$ alkyl and $C_1$-$C_4$ substituted alkyl; $R^4$ is selected from the group consisting of H, $C_1$-$C_4$ alkyl, and $C_1$-$C_4$ substituted alkyl; X is selected from the group consisting of S and O; Z is selected from the group consisting of —$SR^3$ and —$OR^3$; and $R^3$ is selected from the group consisting of H, $C_1$-$C_4$ alkyl, $C_1$-$C_4$ substituted alkyl, and —$CH_2Ph$; and wherein at least two of the $R^2$ and $R^3$ groups in said compound are $C_1$-$C_4$ alkyl when neither Y is the phenyl moiety,
in combination with at least one additional compound selected from the group consisting of salicylates, corticosteroids, immunosuppressants, antibiotics, anti adhesion molecules, and a vitamin D compound,
wherein each substituted $C_1$-$C_4$ alkyl is a $C_1$-$C_4$ alkyl substituted with one or more of:
hydroxyl groups, alkyoxyl groups, carboxyl groups, halogens, nitro groups, amino groups or acylamino groups.

2. The method of claim 1, wherein each substituted $C_1$-$C_4$ alkyl is a $C_1$-$C_4$ alkyl group substituted with groups selected from one or more of hydroxyl groups, alkyoxyl groups, and halogens.

3. The method according to claim 2, wherein the active compound is administered in conjunction with one or more drugs, agents or therapeutics selected from the group consisting of: glucocorticoids, 5-lipoxygenase inhibitors, β-2 adrenoceptor agonists, muscarinic M1 and M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H-3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones.

4. The method according to claim 2, wherein the pharmaceutical composition comprises from about 0.01% to about 25% of the active compound and from about 75% to about 99.99% of a pharmaceutically-acceptable carrier.

5. The method according to claim 1, wherein the active compound has the formula

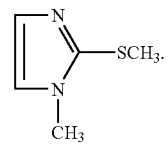

6. The method according to claim 1, wherein the active compound has the formula:

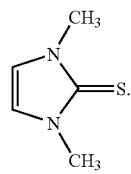

7. The method according to claim 1, wherein the active compound has the formula:

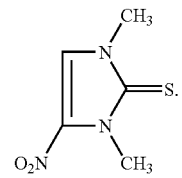

8. The method according to claim 1, wherein the active compound has the formula:

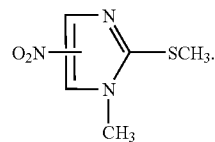

9. The method according to claim 1, wherein Z is $SR^3$ and one of the Y groups is the phenyl moiety.

10. The method according to claim 1, wherein $R^1$ and $R^4$ are H.

11. The method according to claim 1, wherein Z is $SR^3$ and $R^3$ is a methyl, and one of the Y groups is the phenyl moiety wherein $R^1$ and $R^4$ are H, and the $R^2$ group is methyl.

12. The method according to claim 1, wherein one of the Y groups is the phenyl moiety, wherein $R^1$ and $R^4$ are H, and both $R^2$ groups are methyl.

13. The method according to claim 1, wherein the active compound is:

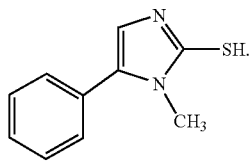

14. The method according to claim 1, wherein the active compound is:

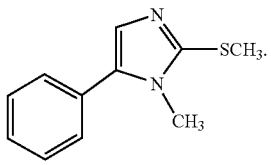

15. The method according to claim 1, wherein the active compound is:

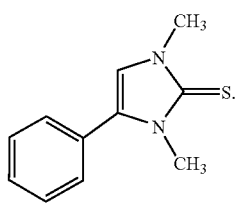

16. A method for the amelioration of episodes of acute or chronic ulcerative colitis in a mammal comprising administering to the mammal a pharmaceutical composition comprising an active compound having the formula selected from the group consisting of:

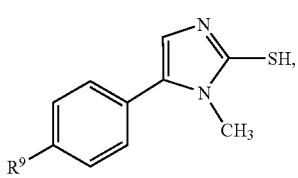

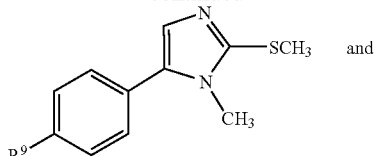

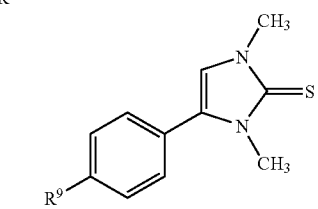

wherein $R^9$ is selected from the group consisting of —OH, —M and —OOCCH$_2$M; and wherein M is selected from the group consisting of F, Cl, Br and I.

17. A method for the amelioration of episodes of acute or chronic ulcerative colitis in a mammal comprising administering to the mammal a pharmaceutical composition comprising an active compound having the formula selected from the group consisting of:

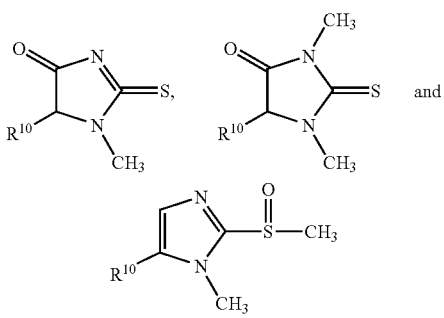

wherein $R^{10}$ is selected from the group consisting of H, —NO$_2$, Ph, 4-HOPh and 4-MPh;

and wherein M is selected from the group consisting of F, Cl, Br and I.

* * * * *